(12) United States Patent
Garibaldi

(10) Patent No.: US 10,062,457 B2
(45) Date of Patent: Aug. 28, 2018

(54) PREDICTIVE NOTIFICATIONS FOR ADVERSE PATIENT EVENTS

(75) Inventor: Federico Garibaldi, Encinitas, CA (US)

(73) Assignee: CareFusion 303, Inc., San Diego, CA (US)

( * ) Notice: Subject to any disclaimer, the term of this patent is extended or adjusted under 35 U.S.C. 154(b) by 179 days.

(21) Appl. No.: 13/559,537

(22) Filed: Jul. 26, 2012

(65) Prior Publication Data
US 2014/0028464 A1 Jan. 30, 2014

(51) Int. Cl.
G08B 23/00 (2006.01)
G16H 50/70 (2018.01)
G16H 50/20 (2018.01)

(52) U.S. Cl.
CPC ............ *G16H 50/70* (2018.01); *G16H 50/20* (2018.01)

(58) Field of Classification Search
CPC ... G06F 19/3443; G06F 19/345; G16H 50/70; G16H 50/20
USPC ....................................... 340/870.02, 870.01
See application file for complete search history.

(56) References Cited

U.S. PATENT DOCUMENTS

| | | |
|---|---|---|
| 2,141,006 A | 12/1938 | Marinsky |
| 3,724,455 A | 4/1973 | Unger |
| 3,831,006 A | 8/1974 | Chaffin, III et al. |
| 3,848,112 A | 11/1974 | Weichselbaum et al. |
| 3,872,448 A | 3/1975 | Mitchell, Jr. |
| 3,898,984 A | 8/1975 | Mandel et al. |
| 3,910,260 A | 10/1975 | Sarnoff et al. |
| 3,921,196 A | 11/1975 | Patterson |
| 3,970,996 A | 7/1976 | Yasaka et al. |
| 4,051,522 A | 9/1977 | Healy et al. |
| 4,135,241 A | 1/1979 | Stanis et al. |
| 4,164,320 A | 8/1979 | Irazoqui et al. |

(Continued)

FOREIGN PATENT DOCUMENTS

| | | |
|---|---|---|
| CA | 2472098 A1 | 7/2003 |
| CA | 2554903 A1 | 4/2005 |

(Continued)

OTHER PUBLICATIONS

International Search Reports and Written Opinions of the International Searching Authority dated Jun. 18, 2014 and Jun. 19, 2014 for PCT applications PCT/US2014/022830, PCT/US2014/022835 and PCT/US2014/022837. Office Action issued in U.S. Appl. Nos. 13/802,683, dated Apr. 29, 2014 and 13/802,433 dated Aug. 25, 2014.

(Continued)

*Primary Examiner* — Naomi J Small
(74) *Attorney, Agent, or Firm* — McDermott Will & Emery LLP

(57) ABSTRACT

Methods for providing predictive notifications to a monitoring device are provided. In one aspect, a method includes receiving retrospective patient data collected from a plurality of medical devices, and determining, based on a comparison of the retrospective patient data with current patient data for a patient from a medical device, a likelihood of a potential adverse medical event occurring for the patient. The method also includes providing a notification to a monitoring device indicative of the potential adverse medical event for the patient. Systems, graphical user interfaces, and machine-readable media are also provided.

23 Claims, 11 Drawing Sheets

(56) References Cited

U.S. PATENT DOCUMENTS

| | | |
|---|---|---|
| 4,216,462 A | 8/1980 | McGrath et al. |
| 4,237,344 A | 12/1980 | Moore |
| 4,315,309 A | 2/1982 | Coli |
| 4,321,461 A | 3/1982 | Walter, Jr. et al. |
| 4,360,125 A | 11/1982 | Martindale et al. |
| 4,373,527 A | 2/1983 | Fischell |
| 4,476,381 A | 10/1984 | Rubin |
| 4,604,847 A | 8/1986 | Moulding, Jr. et al. |
| 4,636,950 A | 1/1987 | Caswell et al. |
| 4,674,652 A | 6/1987 | Aten et al. |
| 4,676,776 A | 6/1987 | Howson |
| 4,688,026 A | 8/1987 | Scribner et al. |
| 4,695,954 A | 9/1987 | Rose et al. |
| 4,696,671 A | 9/1987 | Epstein et al. |
| 4,731,726 A | 3/1988 | Allen |
| 4,733,364 A | 3/1988 | Yamagata |
| 4,741,732 A | 5/1988 | Crankshaw et al. |
| 4,756,706 A | 7/1988 | Kerns et al. |
| 4,778,449 A | 10/1988 | Weber et al. |
| 4,785,969 A | 11/1988 | McLaughlin |
| 4,803,625 A | 2/1989 | Fu et al. |
| 4,810,243 A | 3/1989 | Howson |
| 4,828,545 A | 5/1989 | Epstein et al. |
| 4,831,562 A | 5/1989 | McIntosh et al. |
| 4,835,372 A | 5/1989 | Gombrich et al. |
| 4,839,806 A | 6/1989 | Goldfischer et al. |
| 4,847,764 A | 7/1989 | Halvorson |
| 4,850,009 A | 7/1989 | Zook et al. |
| 4,853,521 A | 8/1989 | Claeys et al. |
| 4,855,909 A | 8/1989 | Vincent et al. |
| 4,857,713 A | 8/1989 | Brown |
| 4,857,716 A | 8/1989 | Gombrich et al. |
| 4,865,584 A | 9/1989 | Epstein et al. |
| 4,882,575 A | 11/1989 | Kawahara |
| 4,899,839 A | 2/1990 | Dessertine et al. |
| 4,916,441 A | 4/1990 | Gombrich et al. |
| 4,918,604 A | 4/1990 | Baum |
| 4,925,444 A | 5/1990 | Orkin et al. |
| 4,942,544 A | 7/1990 | McIntosh et al. |
| 4,950,246 A | 8/1990 | Muller |
| 4,967,928 A | 11/1990 | Carter |
| 4,970,669 A | 11/1990 | McIntosh et al. |
| 4,978,335 A | 12/1990 | Arthur, III |
| 5,001,630 A | 3/1991 | Wiltfong |
| 5,006,699 A | 4/1991 | Felkener et al. |
| 5,036,462 A | 7/1991 | Kaufman et al. |
| 5,036,852 A | 8/1991 | Leishman |
| 5,041,086 A | 8/1991 | Koenig et al. |
| 5,072,383 A | 12/1991 | Brimm et al. |
| 5,077,666 A | 12/1991 | Brimm et al. |
| 5,078,683 A | 1/1992 | Sancoff et al. |
| 5,088,056 A | 2/1992 | McIntosh et al. |
| 5,088,981 A | 2/1992 | Howson et al. |
| 5,100,380 A | 3/1992 | Epstein et al. |
| 5,126,957 A | 6/1992 | Kaufman et al. |
| 5,142,484 A | 8/1992 | Kaufman et al. |
| 5,153,416 A | 10/1992 | Neeley |
| 5,153,827 A | 10/1992 | Coutre et al. |
| 5,164,575 A | 11/1992 | Neeley et al. |
| 5,166,498 A | 11/1992 | Neeley |
| 5,171,977 A | 12/1992 | Morrison |
| 5,181,910 A | 1/1993 | Scanlon |
| 5,190,522 A | 3/1993 | Wojcicki et al. |
| 5,207,642 A | 5/1993 | Orkin et al. |
| 5,235,507 A | 8/1993 | Sackler et al. |
| 5,256,157 A | 10/1993 | Samiotes et al. |
| 5,258,906 A | 11/1993 | Kroll et al. |
| 5,265,010 A | 11/1993 | Evans-Paganelli et al. |
| 5,267,174 A | 11/1993 | Kaufman et al. |
| 5,291,399 A | 3/1994 | Chaco |
| 5,292,029 A | 3/1994 | Pearson |
| 5,307,263 A | 4/1994 | Brown |
| 5,312,334 A | 5/1994 | Hara et al. |
| 5,314,243 A | 5/1994 | McDonald et al. |
| 5,315,505 A | 5/1994 | Pratt et al. |
| 5,317,506 A | 5/1994 | Coutre et al. |
| H1324 H | 6/1994 | Dalke et al. |
| 5,331,547 A | 7/1994 | Laszlo |
| 5,356,378 A | 10/1994 | Doan |
| 5,367,555 A | 11/1994 | Isoyama |
| 5,368,554 A | 11/1994 | Nazarian et al. |
| 5,371,692 A | 12/1994 | Draeger et al. |
| 5,374,813 A | 12/1994 | Shipp |
| 5,376,070 A | 12/1994 | Purvis et al. |
| 5,378,231 A | 1/1995 | Johnson et al. |
| 5,382,232 A | 1/1995 | Hague et al. |
| 5,390,238 A | 2/1995 | Kirk |
| 5,401,059 A | 3/1995 | Ferrario |
| 5,404,384 A | 4/1995 | Colburn et al. |
| 5,408,443 A | 4/1995 | Weinberger |
| 5,412,372 A | 5/1995 | Parkhurst et al. |
| 5,412,564 A | 5/1995 | Ecer |
| 5,416,695 A | 5/1995 | Stutman et al. |
| 5,456,691 A | 10/1995 | Snell |
| 5,460,605 A | 10/1995 | Tuttle et al. |
| 5,465,082 A | 11/1995 | Chaco |
| 5,472,614 A | 12/1995 | Rossi |
| 5,502,944 A | 4/1996 | Kraft et al. |
| 5,515,426 A | 5/1996 | Yacenda et al. |
| 5,522,798 A | 6/1996 | Johnson et al. |
| 5,533,079 A | 7/1996 | Colburn et al. |
| 5,536,084 A | 7/1996 | Curtis et al. |
| 5,538,006 A | 7/1996 | Heim et al. |
| 5,542,420 A | 8/1996 | Goldman et al. |
| 5,544,649 A | 8/1996 | David et al. |
| 5,544,661 A | 8/1996 | Davis et al. |
| 5,547,470 A | 8/1996 | Johnson et al. |
| 5,561,412 A | 10/1996 | Novak et al. |
| 5,562,232 A | 10/1996 | Pearson |
| 5,564,803 A | 10/1996 | McDonald et al. |
| 5,573,506 A | 11/1996 | Vasko |
| 5,582,593 A | 12/1996 | Hultman |
| 5,583,758 A | 12/1996 | McIlroy et al. |
| 5,592,374 A | 1/1997 | Fellagara et al. |
| 5,594,786 A | 1/1997 | Chaco |
| 5,597,995 A | 1/1997 | Williams et al. |
| 5,601,445 A | 2/1997 | Schipper et al. |
| 5,622,429 A | 4/1997 | Heinz |
| 5,628,309 A | 5/1997 | Brown |
| 5,630,710 A | 5/1997 | Tune et al. |
| 5,633,910 A | 5/1997 | Cohen |
| 5,643,212 A | 7/1997 | Coutre et al. |
| 5,644,778 A | 7/1997 | Burks et al. |
| 5,645,531 A | 7/1997 | Thompson et al. |
| 5,651,775 A | 7/1997 | Walker et al. |
| 5,655,118 A | 8/1997 | Hendel et al. |
| 5,657,236 A | 8/1997 | Conkright |
| 5,658,250 A | 8/1997 | Blomquist et al. |
| 5,672,154 A | 9/1997 | Sillen et al. |
| 5,681,285 A | 10/1997 | Ford et al. |
| 5,683,367 A | 11/1997 | Jordan et al. |
| 5,685,844 A | 11/1997 | Marttila |
| 5,689,229 A | 11/1997 | Chaco et al. |
| 5,692,640 A | 12/1997 | Caulfield et al. |
| 5,699,038 A | 12/1997 | Ulrich et al. |
| 5,700,998 A | 12/1997 | Palti |
| 5,703,786 A | 12/1997 | Conkright |
| 5,704,352 A | 1/1998 | Tremblay et al. |
| 5,710,551 A | 1/1998 | Ridgeway |
| 5,712,913 A | 1/1998 | Chaum |
| 5,713,856 A | 2/1998 | Eggers |
| 5,721,913 A | 2/1998 | Ackroff et al. |
| 5,733,259 A | 3/1998 | Valcke et al. |
| 5,737,539 A | 4/1998 | Edelson |
| 5,738,102 A | 4/1998 | Lemelson |
| 5,752,235 A | 5/1998 | Kehr et al. |
| 5,758,095 A | 5/1998 | Albaum et al. |
| 5,758,096 A | 5/1998 | Barsky et al. |
| 5,760,704 A | 6/1998 | Barton et al. |
| 5,764,034 A | 6/1998 | Bowman et al. |
| 5,772,585 A | 6/1998 | Lavin et al. |
| 5,774,865 A | 6/1998 | Glynn |
| 5,781,442 A | 7/1998 | Engelson et al. |
| 5,790,409 A | 8/1998 | Fedor et al. |

(56) References Cited

U.S. PATENT DOCUMENTS

| | | |
|---|---|---|
| 5,795,327 A | 8/1998 | Wilson et al. |
| 5,803,906 A | 9/1998 | Pratt et al. |
| 5,807,321 A | 9/1998 | Stoker et al. |
| 5,807,336 A | 9/1998 | Russo et al. |
| 5,819,229 A | 10/1998 | Boppe |
| 5,822,418 A | 10/1998 | Yacenda et al. |
| 5,822,544 A | 10/1998 | Chaco et al. |
| 5,832,488 A | 11/1998 | Eberhardt |
| 5,833,599 A | 11/1998 | Schrier et al. |
| 5,842,173 A | 11/1998 | Strum et al. |
| 5,842,976 A | 12/1998 | Williamson |
| 5,845,253 A | 12/1998 | Rensimer et al. |
| 5,845,254 A | 12/1998 | Lockwood et al. |
| 5,845,255 A | 12/1998 | Mayaud |
| 5,845,264 A | 12/1998 | Nelhaus |
| 5,848,593 A | 12/1998 | McGrady et al. |
| 5,850,344 A | 12/1998 | Conkright |
| 5,852,408 A | 12/1998 | Christiansen et al. |
| 5,855,550 A | 1/1999 | Lai et al. |
| 5,867,821 A | 2/1999 | Ballantyne et al. |
| 5,871,465 A | 2/1999 | Vasko |
| 5,883,806 A | 3/1999 | Meador et al. |
| 5,885,245 A | 3/1999 | Lynch et al. |
| 5,894,273 A | 4/1999 | Meador et al. |
| 5,895,371 A | 4/1999 | Levitas et al. |
| 5,985,371 A | 4/1999 | Levitas et al. |
| 5,899,998 A | 5/1999 | McGauley et al. |
| 5,903,211 A | 5/1999 | Flego et al. |
| 5,905,653 A | 5/1999 | Higham et al. |
| 5,907,490 A | 5/1999 | Oliver |
| 5,911,132 A | 6/1999 | Sloane |
| 5,911,687 A | 6/1999 | Sato et al. |
| 5,912,818 A | 6/1999 | McGrady |
| 5,920,054 A | 6/1999 | Uber, III |
| 5,920,263 A | 7/1999 | Huttenhoff et al. |
| 5,928,329 A | 7/1999 | Clark et al. |
| 5,930,145 A | 7/1999 | Yuyama et al. |
| 5,935,099 A | 8/1999 | Peterson et al. |
| 5,941,710 A | 8/1999 | Lampotang et al. |
| 5,942,986 A | 8/1999 | Shabot et al. |
| 5,950,630 A | 9/1999 | Portwood et al. |
| 5,950,632 A | 9/1999 | Reber et al. |
| 5,953,099 A | 9/1999 | Walach |
| 5,954,641 A | 9/1999 | Kehr et al. |
| 5,957,885 A | 9/1999 | Bollish et al. |
| 5,961,036 A | 10/1999 | Michael et al. |
| 5,961,446 A | 10/1999 | Beller et al. |
| 5,971,593 A | 10/1999 | McGrady |
| 5,995,077 A | 11/1999 | Wilcox et al. |
| 6,000,828 A | 12/1999 | Leet |
| 6,003,006 A | 12/1999 | Colella |
| 6,009,333 A | 12/1999 | Chaco |
| 6,017,318 A | 1/2000 | Gauthier et al. |
| 6,021,392 A | 2/2000 | Lester et al. |
| 6,024,699 A | 2/2000 | Surwit et al. |
| 6,032,155 A | 2/2000 | de la Huerga |
| 6,039,251 A | 3/2000 | Holowko et al. |
| 6,047,203 A | 4/2000 | Sackner et al. |
| 6,048,087 A | 4/2000 | Laurent et al. |
| 6,053,887 A | 4/2000 | Levitas et al. |
| 6,063,026 A | 5/2000 | Schauss et al. |
| 6,082,776 A | 7/2000 | Feinberg |
| 6,112,182 A | 8/2000 | Akers et al. |
| RE36,871 E | 9/2000 | Epstein et al. |
| 6,135,949 A | 10/2000 | Russo et al. |
| 6,202,923 B1 | 3/2001 | Boyer et al. |
| 6,228,057 B1 | 5/2001 | Vasko |
| 6,241,704 B1 | 6/2001 | Peterson et al. |
| 6,269,340 B1 | 7/2001 | Ford et al. |
| 6,282,441 B1 | 8/2001 | Raymond et al. |
| 6,290,681 B1 | 9/2001 | Brown |
| 6,292,698 B1 | 9/2001 | Duffin et al. |
| 6,302,844 B1 | 10/2001 | Walker et al. |
| 6,312,378 B1 | 11/2001 | Bardy |
| 6,314,556 B1 | 11/2001 | DeBusk et al. |
| 6,319,200 B1 | 11/2001 | Lai et al. |
| 6,322,502 B1 | 11/2001 | Schoenberg et al. |
| 6,338,007 B1 | 1/2002 | Broadfield et al. |
| 6,339,732 B1 | 1/2002 | Phoon et al. |
| 6,406,426 B1 | 6/2002 | Reuss et al. |
| 6,409,684 B1 * | 6/2002 | Wilk ................ A61B 7/00 600/484 |
| 6,421,650 B1 | 7/2002 | Goetz et al. |
| 6,493,747 B2 | 12/2002 | Simmon et al. |
| 6,519,569 B1 | 2/2003 | White et al. |
| 6,529,892 B1 | 3/2003 | Lambert |
| 6,540,672 B1 | 4/2003 | Simonsen et al. |
| 6,558,352 B1 | 5/2003 | Hogan |
| 6,571,128 B2 | 5/2003 | Lebel et al. |
| 6,581,606 B2 | 6/2003 | Kutzko et al. |
| 6,671,563 B1 | 12/2003 | Engelson et al. |
| 6,745,764 B2 | 6/2004 | Hickle |
| 6,757,898 B1 | 7/2004 | Ilsen et al. |
| 6,785,589 B2 | 8/2004 | Eggenberger et al. |
| 6,796,956 B2 | 9/2004 | Hartlaub et al. |
| 6,799,149 B2 | 9/2004 | Hartlaub |
| 6,847,861 B2 | 1/2005 | Lunak et al. |
| 6,856,247 B1 | 2/2005 | Wallace |
| 6,873,268 B2 | 3/2005 | Lebel et al. |
| 6,993,402 B2 | 1/2006 | Klass et al. |
| 7,034,691 B1 | 4/2006 | Rapaport et al. |
| 7,054,844 B2 | 5/2006 | Fletcher et al. |
| 7,060,059 B2 | 6/2006 | Keith et al. |
| 7,096,072 B2 | 8/2006 | Engleson et al. |
| 7,201,734 B2 | 4/2007 | Hickle |
| 7,204,823 B2 | 4/2007 | Estes et al. |
| 7,215,991 B2 | 5/2007 | Besson et al. |
| 7,229,430 B2 | 6/2007 | Hickle et al. |
| 7,230,529 B2 | 6/2007 | Ketcherside, Jr. et al. |
| 7,256,708 B2 | 8/2007 | Rosenfeld et al. |
| 7,263,492 B1 | 8/2007 | Suresh et al. |
| 7,379,885 B1 | 5/2008 | Zakim |
| 7,384,420 B2 | 6/2008 | Dycus et al. |
| 7,398,183 B2 | 7/2008 | Holland et al. |
| 7,421,709 B2 | 9/2008 | Watson et al. |
| 7,433,853 B2 | 10/2008 | Brockway et al. |
| 7,471,994 B2 | 12/2008 | Ford et al. |
| 7,526,769 B2 | 4/2009 | Watts et al. |
| 7,587,415 B2 | 9/2009 | Guarav et al. |
| 7,612,679 B1 | 11/2009 | Fackler et al. |
| 7,693,697 B2 | 4/2010 | Westenskow et al. |
| 7,769,601 B1 | 8/2010 | Bleser et al. |
| 7,771,385 B2 | 8/2010 | Eggers et al. |
| 7,771,386 B2 | 8/2010 | Eggers et al. |
| 7,776,031 B2 | 8/2010 | Hartlaub et al. |
| 7,787,946 B2 | 8/2010 | Stahmann et al. |
| 7,796,045 B2 | 9/2010 | Spear et al. |
| 7,835,927 B2 | 11/2010 | Schlotterbeck et al. |
| 7,847,970 B1 | 12/2010 | McGrady |
| 7,860,583 B2 | 12/2010 | Condurso et al. |
| 7,935,927 B2 | 5/2011 | Miyamoto et al. |
| 7,962,544 B2 | 6/2011 | Torok et al. |
| 7,970,550 B2 | 6/2011 | Arakelyan et al. |
| 8,005,688 B2 | 8/2011 | Coffman et al. |
| 8,024,200 B2 | 9/2011 | Jennings et al. |
| 8,160,895 B2 | 4/2012 | Schmitt et al. |
| 8,291,337 B2 | 10/2012 | Gannin et al. |
| 8,340,792 B2 | 12/2012 | Condurso et al. |
| 8,689,008 B2 | 4/2014 | Rangadass et al. |
| 2001/0037083 A1 | 11/2001 | Hartlaub et al. |
| 2001/0044731 A1 | 11/2001 | Coffman et al. |
| 2002/0010679 A1 | 1/2002 | Felsher |
| 2002/0016568 A1 | 2/2002 | Lebel et al. |
| 2002/0016923 A1 | 2/2002 | Knaus et al. |
| 2002/0022973 A1 | 2/2002 | Sun et al. |
| 2002/0026223 A1 | 2/2002 | Riff et al. |
| 2002/0033548 A1 | 3/2002 | Brodkin et al. |
| 2002/0035484 A1 | 3/2002 | McCormick |
| 2002/0038392 A1 | 3/2002 | De La Huerga |
| 2002/0042636 A1 | 4/2002 | Koshiol et al. |
| 2002/0046346 A1 | 4/2002 | Evans |
| 2002/0077849 A1 | 6/2002 | Baruch et al. |
| 2002/0087114 A1 | 7/2002 | Hartlaub |
| 2002/0116509 A1 | 8/2002 | De La Huerga |

(56) References Cited

U.S. PATENT DOCUMENTS

| | | |
|---|---|---|
| 2002/0120350 A1 | 8/2002 | Klass et al. |
| 2002/0169636 A1 | 11/2002 | Eggers et al. |
| 2002/0198624 A1 | 12/2002 | Greenwald et al. |
| 2003/0009244 A1 | 1/2003 | Engleson et al. |
| 2003/0036683 A1 | 2/2003 | Kehr et al. |
| 2003/0045858 A1 | 3/2003 | Struys et al. |
| 2003/0051737 A1 | 3/2003 | Hickle et al. |
| 2003/0063524 A1 | 4/2003 | Niemiec et al. |
| 2003/0069481 A1 | 4/2003 | Hervy et al. |
| 2003/0105389 A1 | 6/2003 | Noonan et al. |
| 2003/0105555 A1 | 6/2003 | Lunak et al. |
| 2003/0106553 A1 | 6/2003 | Vanderveen |
| 2003/0114836 A1 | 6/2003 | Estes et al. |
| 2003/0121517 A1 | 7/2003 | McFarland |
| 2003/0129578 A1 | 7/2003 | Mault |
| 2003/0135087 A1 | 7/2003 | Hickle et al. |
| 2003/0135388 A1 | 7/2003 | Martucci et al. |
| 2003/0139701 A1 | 7/2003 | White et al. |
| 2003/0140928 A1 | 7/2003 | Bui et al. |
| 2003/0140929 A1 | 7/2003 | Wilkes et al. |
| 2003/0149599 A1 | 8/2003 | Goodall et al. |
| 2003/0156143 A1 | 8/2003 | Westenskow et al. |
| 2003/0158746 A1 | 8/2003 | Forrester |
| 2003/0163223 A1 | 8/2003 | Blomquist |
| 2003/0205897 A1 | 11/2003 | Kaufman |
| 2003/0236683 A1 | 12/2003 | Henderson et al. |
| 2004/0068229 A1 | 4/2004 | Jansen et al. |
| 2004/0073329 A1 | 4/2004 | Engleson et al. |
| 2004/0107118 A1 | 6/2004 | Harnsberger et al. |
| 2004/0122702 A1 | 6/2004 | Sabol et al. |
| 2004/0122705 A1 | 6/2004 | Sabol et al. |
| 2004/0122719 A1 | 6/2004 | Sabol et al. |
| 2004/0122790 A1 | 6/2004 | Walker et al. |
| 2004/0128162 A1 | 7/2004 | Schlotterbeck et al. |
| 2004/0152622 A1 | 8/2004 | Keith et al. |
| 2004/0167465 A1 | 8/2004 | Mihai et al. |
| 2004/0167804 A1 | 8/2004 | Simpson et al. |
| 2004/0172283 A1 | 9/2004 | Vanderveen et al. |
| 2004/0172300 A1 | 9/2004 | Mihai et al. |
| 2004/0172302 A1 | 9/2004 | Martucci et al. |
| 2004/0176297 A1 | 9/2004 | Cheung et al. |
| 2004/0188998 A1 | 9/2004 | Henthorn |
| 2004/0193325 A1 | 9/2004 | Bonderud et al. |
| 2004/0193446 A1 | 9/2004 | Mayer et al. |
| 2004/0260478 A1 | 12/2004 | Schwamm |
| 2005/0010166 A1 | 1/2005 | Hickle |
| 2005/0010269 A1 | 1/2005 | Lebel et al. |
| 2005/0020996 A1 | 1/2005 | Hartlaub et al. |
| 2005/0021297 A1 | 1/2005 | Hartlaub |
| 2005/0022274 A1 | 1/2005 | Campbell et al. |
| 2005/0033606 A1 | 2/2005 | Miller |
| 2005/0049179 A1 | 3/2005 | Davidson et al. |
| 2005/0055242 A1 | 3/2005 | Bello et al. |
| 2005/0088296 A1* | 4/2005 | Lee ............... G08B 21/02 340/539.12 |
| 2005/0096941 A1 | 5/2005 | Tong |
| 2005/0097566 A1 | 5/2005 | Watts et al. |
| 2005/0107914 A1 | 5/2005 | Engleson et al. |
| 2005/0108057 A1 | 5/2005 | Cohen et al. |
| 2005/0113945 A1 | 5/2005 | Engleson et al. |
| 2005/0119788 A1 | 6/2005 | Engleson et al. |
| 2005/0144043 A1 | 6/2005 | Holland et al. |
| 2005/0145010 A1 | 7/2005 | Vanderveen et al. |
| 2005/0148890 A1 | 7/2005 | Hastings |
| 2005/0171815 A1 | 8/2005 | Vanderveen |
| 2005/0224083 A1 | 10/2005 | Crass et al. |
| 2005/0278194 A1 | 12/2005 | Holland et al. |
| 2006/0026205 A1 | 2/2006 | Butterfield |
| 2006/0047538 A1 | 3/2006 | Condurso et al. |
| 2006/0053036 A1 | 3/2006 | Coffman et al. |
| 2006/0079831 A1 | 4/2006 | Gilbert |
| 2006/0101072 A1* | 5/2006 | Busche ............... A61B 5/055 |
| 2006/0122481 A1 | 6/2006 | Sievenpiper et al. |
| 2006/0190302 A1 | 8/2006 | Eggers et al. |
| 2006/0200369 A1 | 9/2006 | Batch et al. |
| 2006/0206356 A1 | 9/2006 | Vanderveen |
| 2006/0217628 A1 | 9/2006 | Huiku |
| 2006/0218015 A1 | 9/2006 | Walker et al. |
| 2006/0229551 A1 | 10/2006 | Martinez et al. |
| 2006/0249423 A1 | 11/2006 | Reijonen |
| 2006/0271401 A1 | 11/2006 | Lassetter et al. |
| 2006/0287890 A1 | 12/2006 | Stead et al. |
| 2007/0015972 A1 | 1/2007 | Wang et al. |
| 2007/0043767 A1 | 2/2007 | Osborne et al. |
| 2007/0061266 A1 | 3/2007 | Moore et al. |
| 2007/0061393 A1 | 3/2007 | Moore |
| 2007/0083389 A1 | 4/2007 | Dyer et al. |
| 2007/0106457 A1 | 5/2007 | Rosenberg |
| 2007/0106753 A1 | 5/2007 | Moore |
| 2007/0106754 A1 | 5/2007 | Moore |
| 2007/0129647 A1* | 6/2007 | Lynn ............... A61B 5/00 600/538 |
| 2007/0156452 A1 | 7/2007 | Batch |
| 2007/0156860 A1 | 7/2007 | Nedelcu et al. |
| 2007/0168301 A1 | 7/2007 | Eisner et al. |
| 2007/0208454 A1 | 9/2007 | Forrester et al. |
| 2007/0210157 A1 | 9/2007 | Miller |
| 2007/0286466 A1 | 12/2007 | Heffernan et al. |
| 2007/0293843 A1 | 12/2007 | Ireland et al. |
| 2008/0015549 A1 | 1/2008 | Maughan |
| 2008/0025230 A1 | 1/2008 | Patel et al. |
| 2008/0034323 A1 | 2/2008 | Blomquist |
| 2008/0040151 A1 | 2/2008 | Moore |
| 2008/0046292 A1 | 2/2008 | Myers et al. |
| 2008/0141272 A1 | 6/2008 | Borgendale et al. |
| 2008/0162254 A1 | 7/2008 | Herger et al. |
| 2008/0164998 A1 | 7/2008 | Scherpbier et al. |
| 2008/0169045 A1 | 7/2008 | Tribble et al. |
| 2008/0195246 A1 | 8/2008 | Tribble et al. |
| 2008/0272138 A1 | 11/2008 | Ross et al. |
| 2008/0317672 A1 | 12/2008 | Viertio-Oja |
| 2009/0012812 A1* | 1/2009 | Rausch ............... G06F 19/322 705/2 |
| 2009/0012813 A1 | 1/2009 | Berzansky |
| 2009/0099867 A1 | 4/2009 | Newman |
| 2009/0112333 A1 | 4/2009 | Sahai |
| 2009/0125335 A1 | 5/2009 | Manetta et al. |
| 2009/0150484 A1 | 6/2009 | Roberts |
| 2009/0210252 A1 | 8/2009 | Silver |
| 2009/0240651 A1 | 9/2009 | Fletcher et al. |
| 2009/0306585 A1 | 12/2009 | Pang et al. |
| 2009/0306944 A1 | 12/2009 | Willmann et al. |
| 2009/0319623 A1 | 12/2009 | Srinivasan et al. |
| 2010/0037067 A1 | 2/2010 | Rangadass et al. |
| 2010/0094653 A1 | 4/2010 | Tribble et al. |
| 2010/0121654 A1 | 5/2010 | Portnoy et al. |
| 2010/0161113 A1 | 6/2010 | Tribble et al. |
| 2010/0169120 A1 | 7/2010 | Herbst et al. |
| 2010/0169771 A1 | 7/2010 | Pelegrin et al. |
| 2010/0174552 A1 | 7/2010 | Hawkes et al. |
| 2010/0174553 A1 | 7/2010 | Kaufman et al. |
| 2010/0179825 A1 | 7/2010 | Hanov et al. |
| 2010/0241453 A1 | 9/2010 | Malec |
| 2010/0241456 A1 | 9/2010 | Miller et al. |
| 2010/0271218 A1 | 10/2010 | Hoag et al. |
| 2010/0280840 A1 | 11/2010 | Fukushi et al. |
| 2010/0323397 A1 | 12/2010 | Reavy et al. |
| 2011/0015941 A1 | 1/2011 | Backhaus |
| 2011/0046975 A1 | 2/2011 | Hoffman |
| 2011/0060758 A1 | 3/2011 | Schlotterbeck et al. |
| 2011/0078608 A1 | 3/2011 | Gannon et al. |
| 2011/0119612 A1 | 5/2011 | Gannon et al. |
| 2011/0179405 A1 | 7/2011 | Dicks et al. |
| 2011/0202495 A1* | 8/2011 | Gawlick ............... A61B 5/0002 706/59 |
| 2011/0282691 A1 | 11/2011 | Coffman et al. |
| 2011/0288882 A1 | 11/2011 | Halow |
| 2011/0313787 A1 | 12/2011 | Rangadass et al. |
| 2012/0011253 A1 | 1/2012 | Friedman et al. |
| 2012/0016215 A1 | 1/2012 | Condurso et al. |
| 2012/0041775 A1 | 2/2012 | Cosentino et al. |
| 2012/0053533 A1 | 3/2012 | Butterfield et al. |
| 2012/0075061 A1 | 3/2012 | Barnes |
| 2012/0136673 A1 | 5/2012 | Presley et al. |

(56) References Cited

U.S. PATENT DOCUMENTS

| | | |
|---|---|---|
| 2012/0173264 A1 | 7/2012 | Brush et al. |
| 2012/0179006 A1* | 7/2012 | Jansen ............... A61B 5/0537 600/301 |
| 2012/0182939 A1 | 7/2012 | Rajan et al. |
| 2012/0185267 A1 | 7/2012 | Kamen et al. |
| 2012/0191052 A1 | 7/2012 | Rao |
| 2012/0239824 A1 | 9/2012 | Nguyen et al. |
| 2012/0241043 A1 | 9/2012 | Perazzo et al. |
| 2012/0247480 A1 | 10/2012 | Varga |
| 2012/0253835 A1 | 10/2012 | Tracy et al. |
| 2012/0265549 A1* | 10/2012 | Virolainen ............ G16H 50/70 705/2 |
| 2013/0018356 A1 | 1/2013 | Prince et al. |
| 2013/0085771 A1 | 4/2013 | Ghanbari et al. |
| 2013/0096444 A1 | 4/2013 | Condurso et al. |
| 2013/0197927 A1 | 8/2013 | Vanderveen et al. |
| 2013/0197928 A1 | 8/2013 | Vanderveen et al. |
| 2013/0197929 A1 | 8/2013 | Vanderveen et al. |
| 2013/0197930 A1 | 8/2013 | Garibaldi et al. |
| 2013/0197931 A1 | 8/2013 | Gupta et al. |
| 2013/0204433 A1 | 8/2013 | Gupta et al. |
| 2013/0204637 A1 | 8/2013 | Vanderveen et al. |
| 2013/0262138 A1 | 10/2013 | Jaskela et al. |
| 2014/0028464 A1 | 1/2014 | Garibaldi |
| 2014/0100868 A1 | 4/2014 | Condurso et al. |
| 2014/0278466 A1 | 9/2014 | Simmons et al. |
| 2014/0297313 A1 | 10/2014 | Condurso et al. |
| 2014/0350950 A1 | 11/2014 | Jaskela et al. |
| 2015/0250948 A1 | 9/2015 | Gupta et al. |
| 2016/0000997 A1 | 1/2016 | Batch et al. |

FOREIGN PATENT DOCUMENTS

| | | |
|---|---|---|
| CN | 1759398 A | 4/2006 |
| CN | 101116077 A | 1/2008 |
| CN | 101146055 A | 3/2008 |
| CN | 201110955 Y | 9/2008 |
| CN | 101331491 A | 12/2008 |
| CN | 101890193 A | 11/2010 |
| CN | 102068725 A | 5/2011 |
| CN | 10 2521394 A | 6/2012 |
| CN | 102508877 A | 6/2012 |
| CN | 102688532 A | 9/2012 |
| CN | 102799783 A | 11/2012 |
| DE | 4023785 | 1/1992 |
| EP | 0192786 | 9/1986 |
| EP | 0384155 | 8/1990 |
| EP | 0595474 | 5/1994 |
| EP | 0649316 | 4/1995 |
| EP | 0652528 | 5/1995 |
| EP | 0784283 | 7/1997 |
| EP | 0921488 | 6/1999 |
| EP | 1003121 | 5/2000 |
| EP | 1018347 | 7/2000 |
| EP | 1237113 | 9/2002 |
| GB | 2141006 | 12/1984 |
| JP | 62114562 | 5/1987 |
| JP | 5168708 | 7/1993 |
| JP | 11-505352 | 5/1999 |
| JP | 2002-520718 | 7/2002 |
| JP | 2003085283 A | 3/2003 |
| JP | 2004287616 A | 10/2004 |
| JP | 2006155070 A | 6/2006 |
| JP | 2008508616 A | 3/2008 |
| KR | 1020070045611 A | 5/2007 |
| KR | 1020080013129 A | 2/2008 |
| KR | 100847397 B1 | 7/2008 |
| KR | 1020100125972 A | 12/2010 |
| KR | 1020110070824 A | 6/2011 |
| KR | 1020120076615 A | 7/2012 |
| KR | 1020120076635 A | 7/2012 |
| NZ | 522631 A | 7/2004 |
| WO | WO1993/022735 | 11/1993 |
| WO | WO1994/005344 | 3/1994 |
| WO | WO1994/008647 | 4/1994 |
| WO | WO1994/013250 | 6/1994 |
| WO | WO1995/023378 | 8/1995 |
| WO | WO1996/020745 | 7/1996 |
| WO | WO-199620745 A1 | 7/1996 |
| WO | WO1996/025214 | 8/1996 |
| WO | WO-199625214 A1 | 8/1996 |
| WO | WO1996/036923 | 11/1996 |
| WO | WO1997/004712 | 2/1997 |
| WO | WO1998/013783 | 4/1998 |
| WO | WO1998/028676 | 7/1998 |
| WO | WO1999/009505 | 2/1999 |
| WO | WO1999/010829 | 3/1999 |
| WO | WO1999/010830 | 3/1999 |
| WO | WO1999/035588 | 7/1999 |
| WO | WO1999/044167 | 9/1999 |
| WO | WO1999/045490 | 9/1999 |
| WO | WO1999/046718 | 9/1999 |
| WO | WO1999/067732 | 12/1999 |
| WO | WO2000/003344 | 1/2000 |
| WO | WO2000/004521 | 1/2000 |
| WO | WO2000/018449 | 4/2000 |
| WO | WO2000/032088 | 6/2000 |
| WO | WO2000/032098 | 6/2000 |
| WO | WO2001/086506 | 11/2001 |
| WO | WO2001/088828 | 11/2001 |
| WO | WO2002/036044 | 5/2002 |
| WO | WO2002/069099 | 9/2002 |
| WO | WO2003/038566 | 5/2003 |
| WO | WO2003/053503 | 7/2003 |
| WO | WO2003/092769 | 11/2003 |
| WO | WO2003/094091 | 11/2003 |
| WO | WO2004/060443 | 7/2004 |
| WO | WO2004/061745 | 7/2004 |
| WO | WO 2010/124016 A1 | 10/2010 |
| WO | WO 2010/124328 A1 | 11/2010 |
| WO | WO-2012095829 A2 | 7/2012 |

OTHER PUBLICATIONS

"'Smart' Infusion Pumps Join CPOE and Bar Coding as Important Ways to Prevent Medication Errors," ISMP—Medication Safety Alert, Feb. 7, 2002, 2 pgs., Institute for Safe Medication Practices.
"General-Purpose Infusion Pumps," Evaluation—Health Devices, Oct. 2002, pp. 353-387, vol. 31(10), ECRI Institute.
"Infusion Pump Technology," Health Devices, Apr.-May 1998, pp. 150-170, vol. 27(4-5), ECRI Institute.
"Infusion Pumps, General-Purpose," Healthcare Product Comparison System, 2007, pp. 1-54, ECRI Institute.
"Infusion Pumps, Large-Volume," Healthcare Product Comparison System, 2010, pp. 1-51, ECRI Institute.
Anonymous, Guardrails® Safety Software—Medley TM Medication Safety System, Alaris Medical Systems XP-00234431; 2002 Alaris Medical Systems Inc. Nov. 2002, SSM @2159C.
Baldauf-Sobez et al., "How Siemens' Computerized Physician Order Entry Helps Prevent the Human Error," Electromedica, vol. 71, No. 1, 2003, pp. 2-10.
Calabrese, et al., "Medication administration errors in adult patients in the ICU," Intensive Care Med, 2001, pp. 1592-1598, vol. 27, Springer-Verlag.
Eskew, James et al., Using Innovative Technologies to Set New Safety Standards for the Infusion of Intravenous Medications, Hospital Pharmacy, vol. 37, No. 11, pp. 1179-1189, 2002, Facts and Comparisons.
Kohn, et al., "To Err is Human—Building a Safer Health System," National Academy Press, 2002, pp. i-287, National Academy of Sciences.
Lesar, "Recommendations for Reducing Medication Errors," Medscape Pharmacists, posted Jul. 24, 2000, 10 pgs, vol. 1(2), Medscape Pharmacists, <http://www.medscape.com>.
Meier, "Hospital Products Get Seal of Approval at a Price," The New York Times, Apr. 23, 2002, 5 pgs.
Shabot, et al., "Wireless clinical alerts for critical medication, laboratory and physiologic data," System Sciences 2000. Proceedings of the 33rd Annual Conference on Jan. 4-7, 2000, Piscataway, NJ, IEEE, Jan. 4, 2000.

(56) References Cited

OTHER PUBLICATIONS

Williams, et al., "Reducing the Risk of User Error with Infusion Pumps," Professional Nurse—Safe Practice—Infusion Devices, Mar. 2000, pp. 382-384, vol. 15(6).
Yokoi, "Prevention of Errors in Injection/Drip Infusion—No excuse for ignorance!—Essential Points of Accident Prevention, IV Infusion Pump, Syringe-pump Accident Prevention," JIN Special, Igaku Shoin K.K., Dec. 1, 2001, pp. 109-120, No. 70.
International Search Reports and Written Opinions of the International Searching Authority dated Jun. 19, 2014 and Jun. 24, 2014 for PCT Application Nos. PCT/US2014/022840 and PCT/US2014/022832.
Non-Final Office Action dated Oct. 14, 2014, issued in U.S. Appl. No. 11/326,145.
U.S. Appl. No. 90/009,912, filed Aug. 12, 2013, Schlotterbeck et al.
U.S. Appl. No. 90/011,697, filed Aug. 12, 2013, Schlotterbeck et al.
International Search Report and Written Opinion for Application No. PCT/US2013/050732, dated Feb. 4, 2014, 9 pages.
Queensland Health. Use of returned or unused dispensed medicines, Jan. 5, 2005, Queensland Government. pp. 1-2.
U.S. Appl. No. 13/901,501, filed May 23, 2013.
International Search Report and Written Opinion of the International Searching Authority dated Sep. 5, 2014 for PCT application PCT/US2014/037577.
Evans, R. S. et al., "Enhanced notification of infusion pump programming errors", Studies in health technology and informatics, Jan. 1, 2010, pp. 734-738, XP055305644, Netherlands DOI: 10.3233/978-1-60750-588-4-734 Retrieved from the Internet: URL:http://booksonline.iospress.nl/Extern/EnterMedLine.aspx?ISSN=0926-9630&Volume=160&SPage=734 [retrieved on Sep. 26, 2016].
Extended European Search Report and Written Opinion for Application No. 14772937.0, dated Oct. 10, 2016, 9 pages.
Extended European Search Report and Written Opinion for Application No. 14779139.6, dated Nov. 7, 2016, 7 pages.
Extended European Search Report for Application No. 14775918.7, dated Sep. 13, 2016, 10 pages.
Extended European Search Report for Application No. 14779655.1, dated Jul. 14, 2016, 8 pages.
Extended European Search Report for Application No. 14780320.9, dated Jul. 1, 2016, 7 pages.
Canadian Office Action for Application No. 2512991, dated Mar. 2, 2017, 4 pages.
Extended European Search Report for Application No. 14801713.0, dated Jan. 16, 2017, 8 pages.
Extended European Search Report for Application No. 14801726.2, dated Jan. 5, 2017, 8 pages.
Chinese Office Action for Application No. 201480015147.6, dated Mar. 10, 2017, 10 pages excluding translation.
Chinese Office Action for Application No. 201480015025.7, dated Jan. 23, 2018, 11 pages excluding English summary.
Chinese Office Action for Application No. 201480015036.5, dated Jan. 23, 2018, 13 pages excluding English translation.
European Office Action for Application No. 14779655.1, dated Mar. 8, 2018, 7 pages.
Japanese Office Action in Application No. 2016-501081, dated Feb. 9, 2018, 4 pages.
Memo concerning Mexican Office Action for Application No. MX/a/2015/015959, memo dated Mar. 2, 2018, 1 page.
Canadian Office Action for Application No. 2512991, dated Jan. 10, 2018, 4 pages.
Canadian Office Action for Application No. 2828898, dated Jan. 11, 2018, 8 pages.
Australian Examination Report No. 1 for Application No. 2016216550, dated Sep. 20, 2017, 3 pages.
Chinese Office Action for Application No. 201480015147.6, dated Nov. 16, 2017, 8 pages.
European Communication of the Board of Appeal for Application No. 05791269.3, dated Nov. 10, 2017, 7 pages.
European Office Action for Application No. 14775918.7, dated Dec. 20, 2017, 8 pages.
Canadian Office Action for Application No. 2551903, dated Mar. 28, 2017, 7 pages.
European Office Action for Application No. 12756903.6, dated Apr. 19, 2017, 5 pages.
Office Action for United Arab Emirates Application No. UAE/P/0962/2013, dated Apr. 17, 2017, 18 pages.
European Office Action for Application No. 14779655.1, dated Jul. 28, 2017, 6 pages.
Memo concerning Mexican Office Action for Application No. MX/a/2015/015959, dated Sep. 21, 2017, 4 pages.
Canadian Office Action for Application No. 2551903, dated Mar. 5, 2018, 8 pages.
Chinese Office Action for Application No. 201480015147.6, dated May 3, 2018, 6 pages.
European Office Action for Application No. 14772937.0, dated Apr. 19, 2018, 9 pages.

\* cited by examiner

| Adverse Event | $CO_2$ Level | $O_2$ Level | $O_2$ Level | HR Value | |
|---|---|---|---|---|---|
| Apnea | < 50 % | 60% - 88% | | < 50 bpm | |
| Seizure | < 50 % | <60 % | | N/A | |
| ... | | | | | |

FIG. 4A

Pharmacy Logistics

Infusion Viewer

PHARMACY DASHBOARD | Infusions | Preferences | Users | Help | Manual | About

Show: ☑ Infusing ☑ Stopped ☑ Completed ☑ Disconnected    Filter: ☐ My Filter ☐ No Patient ID ☐◯ ☐△ More Filters Show [15 ▼] Infusions Show / hide columns

| Patient ID | Profile | Infusion Name | Drug Amt/Diluent Vol | VTBI | Alerts | Cumulative Volume Infused | Dose | Rate | (est.) Time until Empty | (est.) Volume Remaining | Infusion Status | Last Update | High Priority |
|---|---|---|---|---|---|---|---|---|---|---|---|---|---|
| RA122331 | NICU | TPN ⓖ | N/A | 115 mL | △ | 810.8 ml | N/A | 5.2 mL/hr | 22 hr | 115 mL | Infusing | 6/12/2011 16:45 | ☑ |
| BU453627 | Adult ICU | Cyclosporine | 450 mg/250 mL | 10 mL | △ | 5.3 ml | 1 mg/min | 33.3 mL/hr | 7 hr | 235 mL | Infusing | 6/12/2011 16:45 | ☑ |
| JO886412 | Adult ICU | Vancomycin | 1000 mg/200 mL | 50 mL | | | 100 mg | 250 mL/hr | 12 min | 50 mL | Infusing | 6/12/2011 16:45 | ☐ |
| XY081783 | Med/Surg | 0.9% NS | N/A | 235 mL | | | N/A | 75 mL/hr | 3 hr 13 min | 235 mL | Infusing | 6/12/2011 16:45 | ☐ |
| NV125574 | Med/Surg | Insulin | 100 units/100 m | 10 mL | | | 13 units/hr | 13 mL/hr | 5 hr | 65 mL | Stopped | 6/12/2011 16:45 | ☐ |
| TR164533 | Adult ICU | Dopamine | 400 mg/250 mL | 225 mL | | | 15 mcg/kg/min | 33.9 mL/hr | 6 hr 54 min | 235 mL | Infusing | 6/12/2011 16:45 | ☐ |
| (unknown) | Adult ICU | Alteplase | 100 mg/100 mL | 75 mL | | | 50 mg/hr | 50 mL/hr | 45 min | 75 mL | Infusing | 6/12/2011 16:45 | ☐ |
| PO788854 | Oncology | Paclitaxel | 263 mg/500 mL | 500 mL | | | 263 mg | 167 mL/hr | 3 hr | 497 mL | Stopped | 6/12/2011 16:45 | ☐ |
| MN124311 | L&D | Vancomycin | 500 mg/150mL | 100 mL | | | N/A | 100 mL/hr | 1 hr | 100 mL | Infusing | 6/12/2011 16:45 | ☐ |
| IU986342 | L&D | Magnesium Sulfate | 40 gram/ 1000 mL | 100 mL | | | 2 gram/hr | 50 L/hr | 19 hr | 950 mL | Infusing | 6/12/2011 16:45 | ☐ |
| (unknown) | Peds ICU | D5 1/2NS + KCl 20mEq | N/A | 400 mL | | | N/A | 50 mL/hr | 8 hr | 400 mL | Stopped | 6/12/2011 16:45 | ☐ |
| (unknown) | Med/Surg | Unknown | N/A | 300 mL | | | N/A | 100 mL/hr | 3 hr | 300 mL | Infusing | 6/12/2011 16:45 | ☐ |

Showing 1 to 12 of 12 Infusions    First Previous 1 Next Last

FIG. 4B

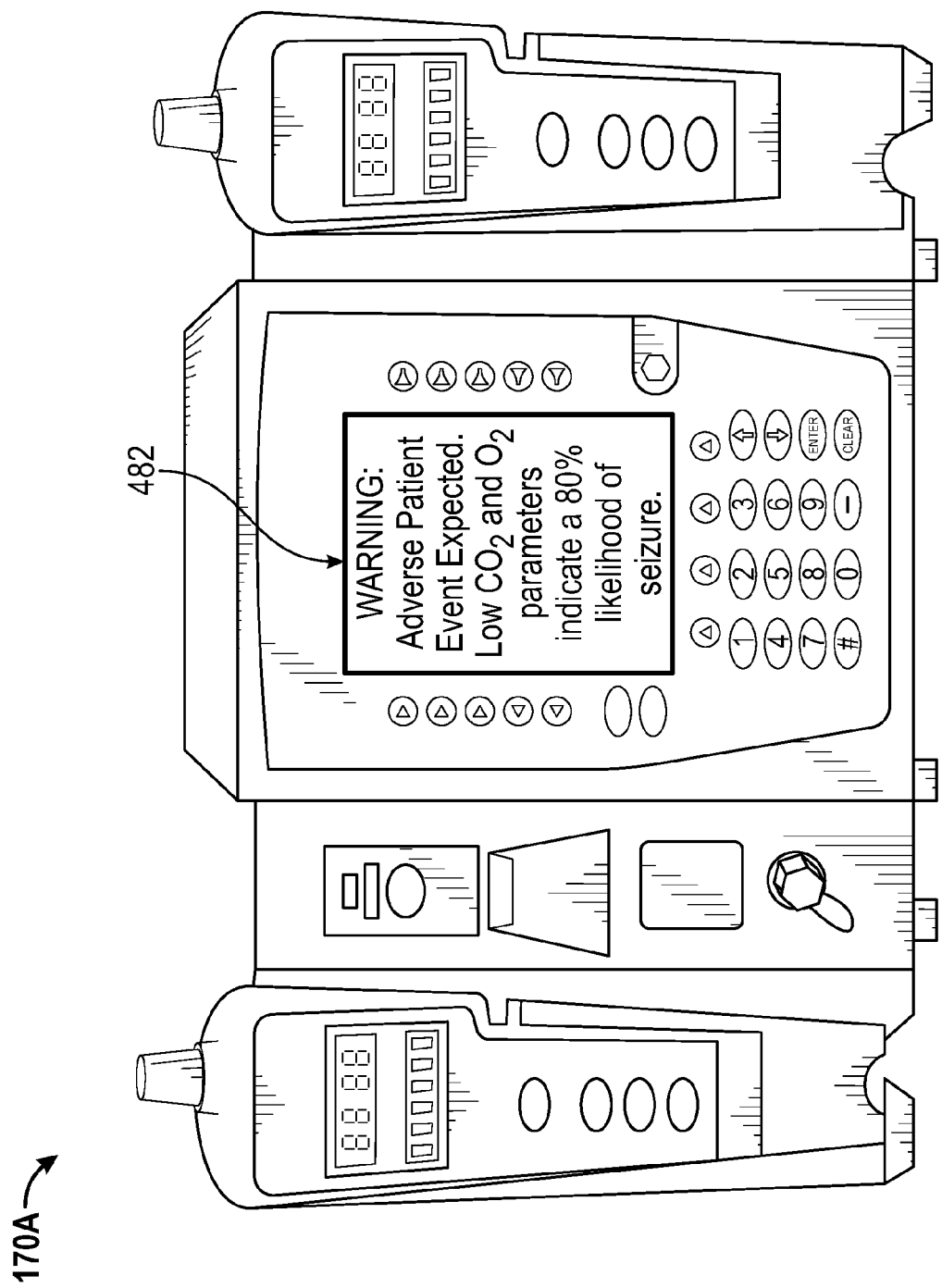

PREDICTIVE NOTIFICATIONS FOR ADVERSE PATIENT EVENTS

BACKGROUND

Field

The present disclosure generally relates to medical devices, and particularly to providing notifications to medical devices.

Description of the Related Art

A medical device, such as an infusion pump system, ventilator system, or physiological statistic (e.g., vital sign) monitor, commonly includes a display of real-time (or near real-time) data on a patient, such as a medication infusion status of the patient or vital signs of the patient. Such medical devices may provide the real-time patient data to a server for storage. The server can collect data from one or many medical devices for storage as retrospective patient data. As a result, two forms of patient data are commonly available at the same time: real-time patient data and retrospective patient data.

SUMMARY

According to one embodiment of the present disclosure, a hospital administration system for providing predictive notifications to a monitoring device is provided. The system includes a memory and a processor. The memory includes retrospective patient data collected from a plurality of medical devices. The processor is configured to determine, based on a comparison of the retrospective patient data with current patient data for a patient from a medical device, a likelihood of a potential adverse medical event occurring for the patient. The processor is also configured to provide a notification to a monitoring device indicative of the potential adverse medical event for the patient.

According to another embodiment of the present disclosure, a method for providing predictive notifications to a monitoring device is provided. The method includes receiving retrospective patient data collected from a plurality of medical devices, and determining, based on a comparison of the retrospective patient data with current patient data for a patient from a medical device, a likelihood of a potential adverse medical event occurring for the patient. The method also includes providing a notification to a monitoring device indicative of the potential adverse medical event for the patient.

According to a further embodiment of the present disclosure, a machine-readable storage medium includes machine-readable instructions for causing a processor to execute a method for providing predictive notifications to a monitoring device is provided. The method includes receiving retrospective patient data collected from a plurality of medical devices, and determining, based on a comparison of the retrospective patient data with current patient data for a patient from a medical device, a likelihood of a potential adverse medical event occurring for the patient. The method also includes providing a notification to a monitoring device indicative of the potential adverse medical event for the patient.

It is understood that other configurations of the subject technology will become readily apparent to those skilled in the art from the following detailed description, wherein various configurations of the subject technology are shown and described by way of illustration. As will be realized, the subject technology is capable of other and different configurations and its several details are capable of modification in various other respects, all without departing from the scope of the subject technology. Accordingly, the drawings and detailed description are to be regarded as illustrative in nature and not as restrictive.

BRIEF DESCRIPTION OF THE DRAWINGS

The accompanying drawings, which are included to provide further understanding and are incorporated in and constitute a part of this specification, illustrate disclosed embodiments and together with the description serve to explain the principles of the disclosed embodiments. In the drawings:

FIGS. 4A-4C are example illustrations associated with the example processes of FIGS. 3A and 3B.

DETAILED DESCRIPTION

In the following detailed description, numerous specific details are set forth to provide a full understanding of the present disclosure. It will be apparent, however, to one ordinarily skilled in the art that the embodiments of the present disclosure may be practiced without some of these specific details. In other instances, well-known structures and techniques have not been shown in detail so as not to obscure the disclosure.

The disclosed system uses retrospective patient data obtained from multiple medical devices as real-time (or near real-time) patient data, and analyzes the retrospective patient data for common patterns or values that resulted in the occurrence of a potential adverse medical event, such as a heart attack, seizure, or stroke. The identified patterns and/or values are then compared to real-time patient data being received from a medical device in order to determine whether a similar pattern and/or value appears in the real-time patient data. If such a similar pattern and/or value appears, thereby indicating an increased likelihood of a potential adverse medical event, a notification is provided to a monitoring device (or "central monitor") that is being viewed by a person, such as a pharmacist or physician. A notification can also be provided to the medical device.

As discussed herein, real-time data and near real-time data denote information that is delivered immediately after collection. There is little to no delay in the timeliness of the information provided. Both real-time patient data and near real-time patient data are referred to herein as "real-time patient data." Real-time patient data can be patient data that is recorded for a patient within at least one of a past 5 seconds, 10 seconds, 15 seconds, 30 seconds, one minute, two minutes, five minutes, ten minutes, thirty minutes, or an hour.

Figure 1:
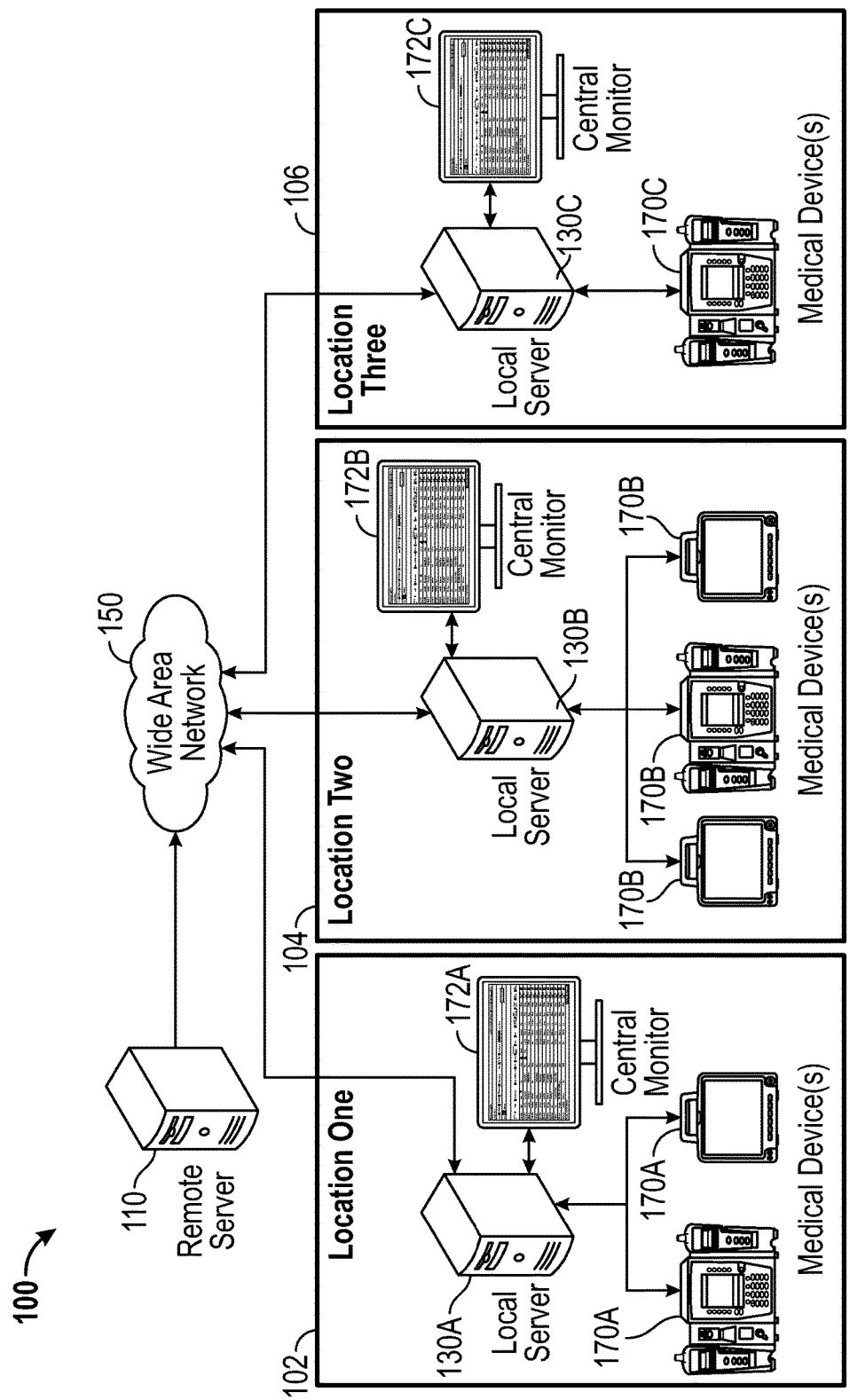
FIG. 1 illustrates an example architecture for providing predictive notifications to a monitoring device.

Referring now to the drawings, FIG. 1 illustrates an example architecture 100 for providing predictive notifications to a monitoring device. The architecture 100 includes a remote server 110 connected over a network 150 to local servers 130A-C, central monitors 172A-C, and medical devices 170A-C at three different locations 102, 104, and 106, representing three different health institutions.

Although three locations 102, 104, and 106 are illustrated in the example architecture 100, more or fewer locations are also within the scope of the disclosure. Additionally, while each location 102, 104, and 106 is illustrated as having a single local server 130A-C (respectively) and between one to three medical devices 170A-C, each location can also have multiple local servers and a large number of medical devices. Accordingly, the architecture 100 of FIG. 1 is provided as an example only to indicate that the remote server 110 collects data from a plurality of locations, and is not intended to limit the scope or particular configuration of the disclosed system. The example locations are not limited to physical locations, but instead each location can be associated with an entity. For example, location one 102 can be associated with a first health care entity in a first geographical location, while medical device 170A associated with location one 102 can be physically located in a second geographical location, such as a patient's home.

The example locations 102, 104, and 106 can be, for example, different hospitals or health care institutions within a city, state, country, or across countries. For example, a first location 102 in Dodge City for Dodge City Hospital can include two infusion pumps 170-A in Building A, which is located in a northern region of Dodge City. A second location 104 in Dodge City for Dodge City Hospital can include three physiological statistic monitors 170-B in Building B, located in a southern region of Dodge City five miles away from Building A. A third location in Dodge City for Dodge City Hospital can include an infusion pump 170-C in Building C, located in a western region of Dodge City ten miles away from both Building A and Building B. The medical devices 170 of Buildings A, B, and C, however, are each connected to the network 150 and provide real-time patient data, such as physiological values (e.g., $CO_2$ levels, heart rates) and adverse medical events (e.g., date, time, and type of adverse medical event experienced, such as a heart attack or seizure) to their respective local servers 130A-C. The network 150 can include, for example, any one or more of a personal area network (PAN), a local area network (LAN), a campus area network (CAN), a metropolitan area network (MAN), a wide area network (WAN), a broadband network (BBN), the Internet, and the like. Further, the network 150 can include, but is not limited to, any one or more of the following network topologies, including a bus network, a star network, a ring network, a mesh network, a star-bus network, tree or hierarchical network, and the like.

Each of the local servers 130A-C is configured to collect real-time patient data from its respective medical devices 170A-C over a local area network and store the data as local medical device data. The medical devices 170A-C can be, for example, infusion pump systems, ventilator systems and other respiratory care systems, or physiological statistic monitors (e.g., vital sign monitors). Although infusion pump systems and physiological statistic monitors are illustrated and referred to in the examples described herein, any other medical device 170 having an appropriate processor, memory, and communications capabilities for connecting to the local servers 130A-C and providing real-time patient data can be used. Each local server 130A-C is also configured to provide the collected real-time patient data to the remote server 110, which, when provided with the real-time patient data from each medical device 170A-C, stores the real-time patient data for each medical device as retrospective patient data. Retrospective patient data can be patient data that is older than one day, for example.

In certain aspects, the remote server 110 then provides the retrospective patient data to each of the local servers 130A-C. The local servers 130A-C each process the retrospective patient data to identify patterns and/or values in the retrospective patient data that indicate a potential adverse patient medical event, such as a heart attack or stroke. Each of the local servers 130A-C then stores the identified patterns as pattern data on the local servers 130A-C.

In certain aspects, the remote server 110 identifies patterns and/or values in the retrospective patient data that indicate a potential adverse patient medical event, such as a heart attack or stroke, and stores the identified data locally as pattern data on the remote server 110. The remote server 130 then provides the pattern data to each of the local servers 130A-C for storage.

Each of the local servers 130A-C can compare the pattern data with real-time patient data being received by medical devices 170A-C connected to each of the local servers 130A-C. The comparison can be made using, for example, pattern matching algorithms. If the comparison of the pattern data with the real-time patient data indicates that a potential adverse patient medical event is likely to occur, then the local servers 130A-C send a notification to a monitoring device or "central monitor" 172A. The central monitor 172A can be, for example, a console or display in a centralized area of the corresponding location 102, 104, and 106, and can be monitored by a person, such as a pharmacist or physician. The notification is indicative of the adverse patient medical event and can be displayed on the corresponding medical device 170A-C associated with the patient, and additionally displayed on another device (e.g., an administrator's device, such as a pharmacist console) in order to facilitate a proper response to the potential adverse patient medical event.

The local servers 130A-C can be devices having an appropriate processor, memory, and communications capability for hosting local medical device data, pattern data, and a pattern comparison interface and/or pattern recognition interface. The remote server 110 can be a device having an appropriate processor, memory, and communications capability for hosting collected medical device data, pattern data, and a pattern recognition interface.

Figure 2A:
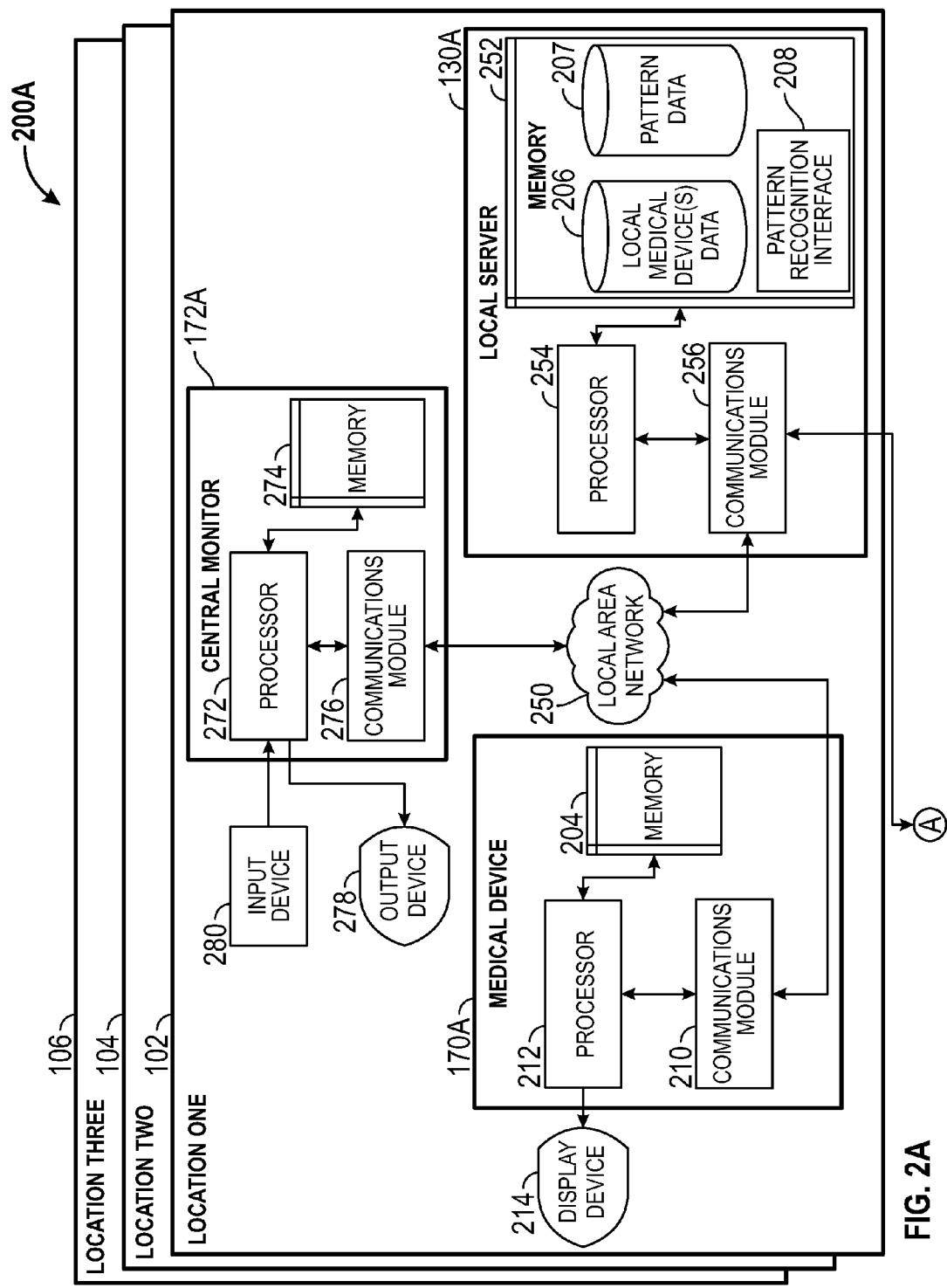
FIGS. 2A and 2B are block diagrams illustrating an example medical device, central monitor, local server, and remote server from the architecture of FIG. 1 according to certain aspects of the disclosure.
Figure 2A:
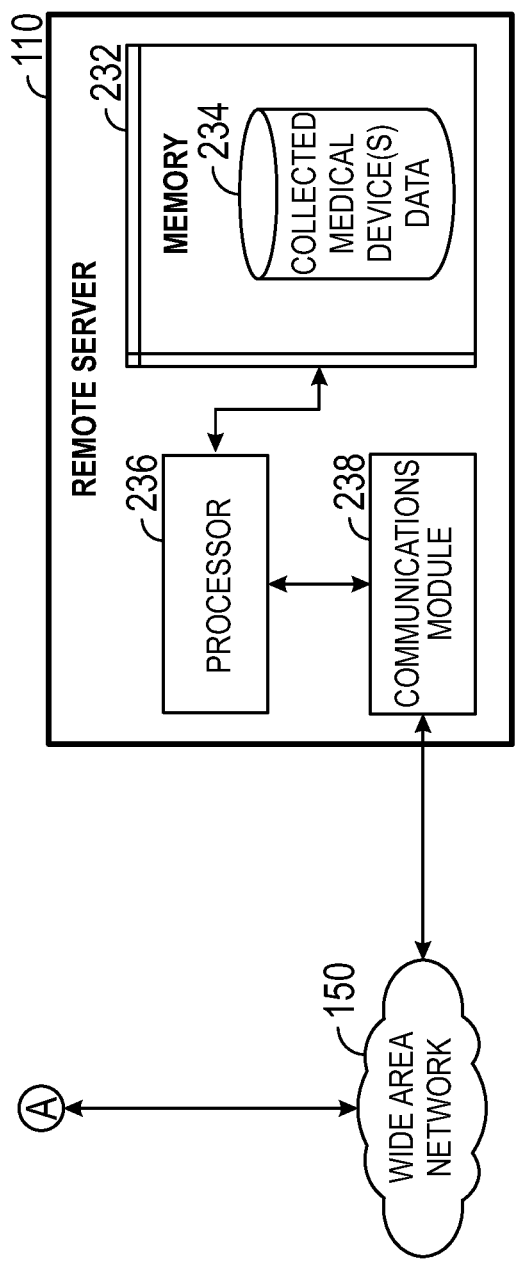
Figure 2B:
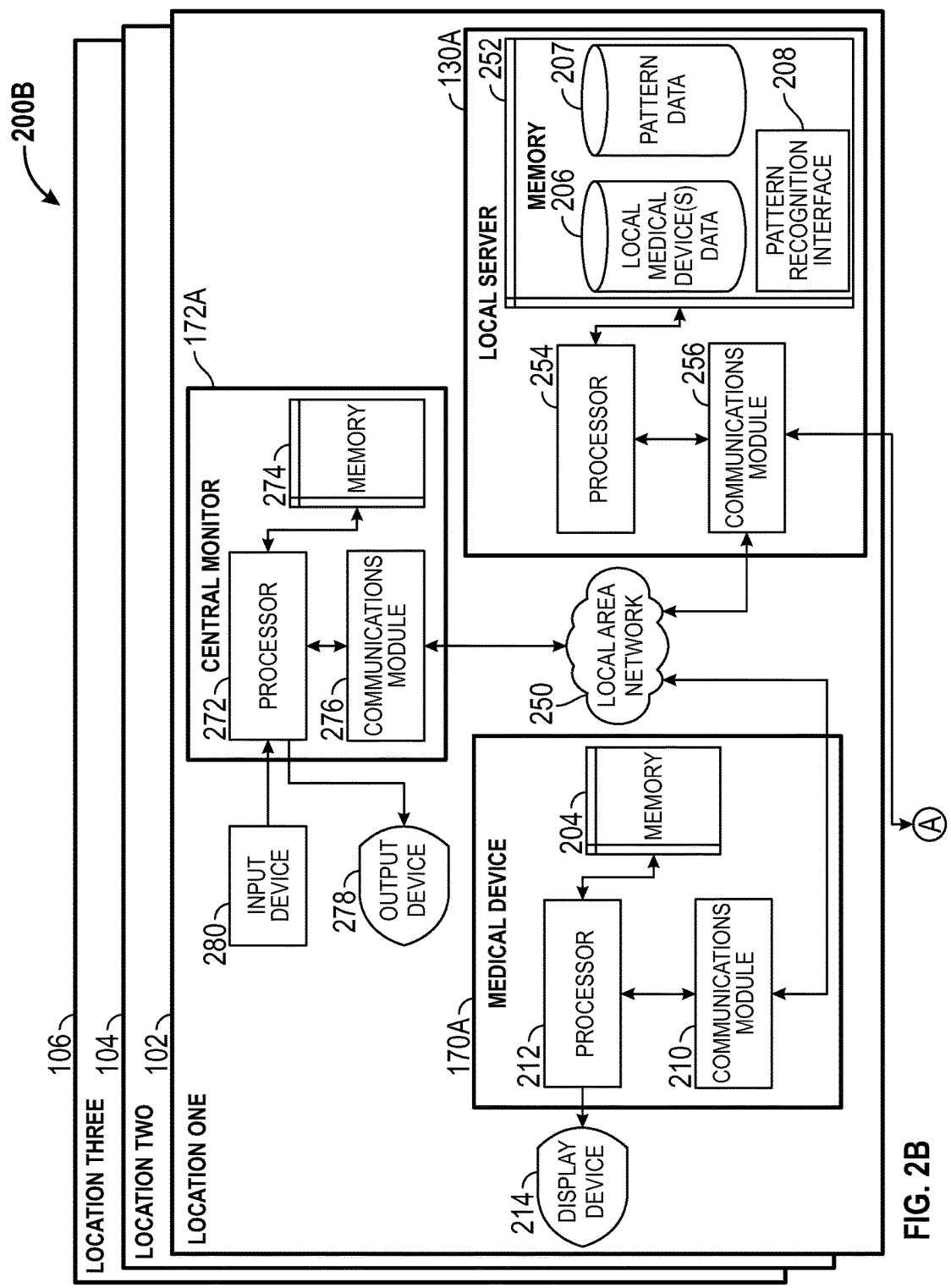
Figure 2B:
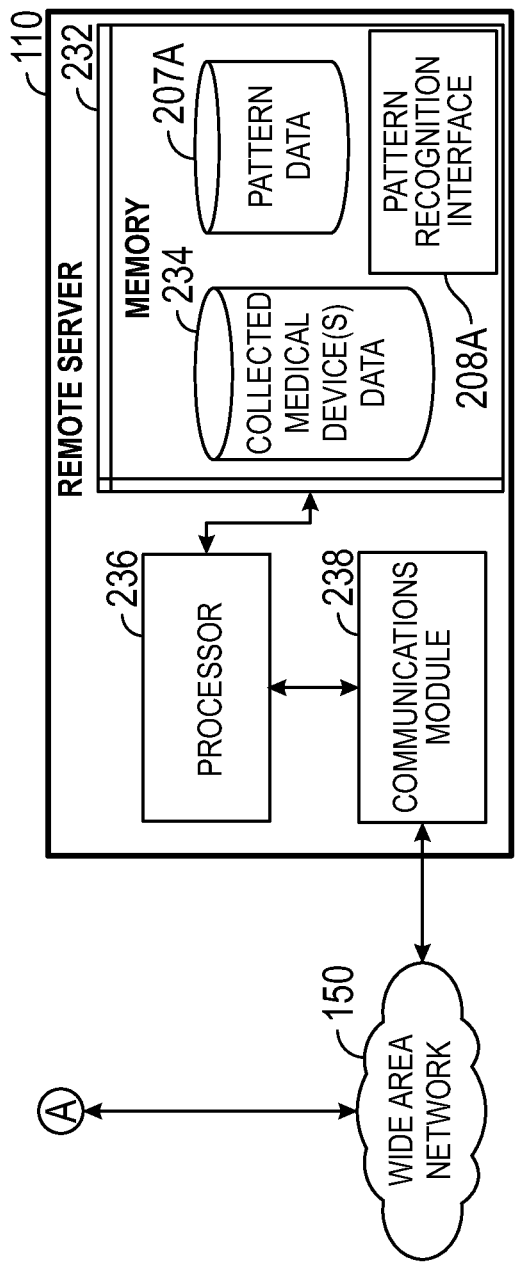

FIGS. 2A and 2B are block diagrams 200A and 200B illustrating an example medical device, central monitor, local server, and remote server from the architecture of FIG. 1 according to certain aspects of the disclosure. In the block diagram 200A of FIG. 2A, the pattern recognition interface 208 is located on the local server 130A, and in the block diagram 200B of FIG. 2B, the pattern recognition interface is located on the remote server 110.

With reference to FIG. 2A, the block diagram 200 includes a medical device 170A at location one 102 connected to a local server 130A at location one 102 by a local area network 250. The local server 130A is also connected to a central monitor 172A. A remote server 110 is connected to the local server 130A of location one 102 over a wide area network 150. Although location one 102 is illustrated in detail, locations two 104 and three 106 are also represented and can be configured in accordance with the description provided for location one 102 as each of locations two 104 and three 106 are also connected to the remote server 110. The medical device 170A, the central monitor 172A, the local server 130A, and the remote server 110 are each connected over their respective networks 250 and 150 via respective communications modules 210, 276, 256, and 238. The communications modules 210, 276, 256, and 238 are configured to interface with the networks 250 and 150 to send and receive information, such as data, requests, responses, and commands to other devices on the network. The communications modules 210, 276, 256, and 238 can be, for example, modems or Ethernet cards.

The local server 130A includes a processor 254, the communications module 256, and a memory 252 that includes local medical device(s) data 206, pattern data 207, and a pattern recognition interface 208. The processor 254 of the local server 130A is configured to execute instructions, such as instructions physically coded into the processor 254, instructions received from software in memory 252, or a combination of both. For example, the processor 254 of the local server 130A executes instructions to receive real-time patient data from each medical device 170A connected to the local server 130A in location one 102 over the local area network 250. The real-time patient data can be, for example, information on medication being provided to a patient or a physiological statistic of a patient. Exemplary information on a medication being provided to a patient can include, but is not limited to, information indicating the medication name, medication dose, medication administration rate, time at which the medication was first administered, the amount of medication administered to the patient so far, expected time at which the medication is expected to complete administration, the amount of medication remaining, a medication administration schedule, medication administration profile, an identifier of the patient receiving the medication, medical condition, and medication administration status. The physiological statistics of the patient can include, for example, $CO_2$ level, $O_2$ level, heart (e.g., pulse) rate, blood pressure, respiratory rate, body temperature, blood glucose level, oxygen saturation, $CO_2$ degree of change over time, and $O_2$ degree of change over time, race of the patient, gender of the patient, age of the patient, and adverse medical event history for the patient.

The processor 254 of the local server 130A provides the real-time patient data to the remote server 110 over the wide area network 150. The real-time patient data can be provided by the local server 130A to the remote server 110 according to a schedule. The real-time patient data can also be provided by the local server 130A to the remote server 110 in response to a request from the remote server 110 for the real-time patient data.

The remote server 110, which includes a processor 236, the communications module 238, and a memory 232, receives the real-time patient data using the processor 236 from the local server 130A at location one 102 and any other local servers 130B and 130C (e.g., at locations two and three 104 and 106). The remote server 110 stores the real-time patient data from the local servers 130A-C in memory 232 as collected medical device(s) data 234 (or "retrospective patient data" 234). The processor 236 of the remote server 110 then executes instructions, such as instructions physically coded into the processor 236, instructions received from software in memory 232, or a combination of both, to provide the collected medical device data 234 to the local server 130A. In certain aspects, the entire collected medical device data 234 can be provided to the local server 130A. In certain aspects, a subset of the collected medical device data 234 can be provided to the local server 130A, such as data for values that are more indicative of adverse patient medical events.

The processor 254 of the local server 130A executes instructions to receive (e.g., from the remote server 110) the collected medical device data 234 from the medical devices 170A-C, and determine, using pattern recognition interface 208 to compare the collected medical device data 234 with current patient data for a patient from a medical device 170A, a likelihood of a potential adverse medical event occurring for the patient. The processor 254 then executes instructions to provide a notification indicative of the potentially adverse medical event to the central monitor 172A. Specifically, notification is provided by the local server 130A over the local area network 250 to the processor 272 of the central monitor 172A using respective communications modules 256 and 276 of the local server 130A and central monitor 172A. The notification is displayed on the output device 278 (e.g., display) of the central monitor, and additional information regarding the notification can be obtained by a user using the input device 280 of the central monitor 172A. The notification can be stored in a memory 274 of the central monitor 172A. The notification can include, for example, information indicating the likelihood of the potentially adverse medical event occurring for the patient, a description of the potentially adverse medical event, a description of a cause for the occurrence of the potentially adverse medical event, and/or information on how to configure the medical device in order to reduce the occurrence of the potentially adverse medical event.

The determination of the likelihood of the potentially adverse medical event occurring for the patient can be made using a pattern matching algorithm. The pattern matching algorithm can be based on, for example, keypoint matching, elementary image processing, histogram matching, string searching, approximate string matching (or "fuzzy string searching"). For example, with keypoint matching, several scale-invariant feature transform (SIFT) points can be selected from the collected medical device data 234, and the SIFT points can be compared with corresponding points in the real-time patient data from the medical device 170A. With elementary image processing, one or many reference patterns can be obtained by scanning a graph or other image representing the collected medical device data. The reference patterns can be compared with patterns from the real-time patient data. With histogram matching, a histogram value representing a histogram of the collected medical device data 234 can be compared with a histogram value representing the real-time patient data. If the two histogram values are the same or within a certain range of another, then a pattern match is indicated. For both string searching and approximate string matching, a string of values or other data from the collected medical device data 234 can be compared with corresponding value or data from the real-time patient data to determine whether the values or data match or are within a certain predetermined range of one another.

In certain aspects, a pattern match includes identifying at least two parameters in the current patient data for the patient that are equal to or within a certain predetermined range of values in the collected medical device data 234, or identifying a trend that is substantially similar between the current patient data for the patient and the collected medical device data 234. For example, if the collected medical device data 234 indicates a $CO_2$ level value of 50% and an $O_2$ level value of 60% indicates a potential adverse patient medical event of apnea, then a pattern match is indicated if the real-time patient data matches or is within 5% of the corresponding $CO_2$ level value of 50% and an $O_2$ level value of 60%. In certain aspects, a speed or rate of change at which a parameter value varies is also considered in determining whether a pattern match is indicated.

The block diagram 200B of FIG. 2B and the corresponding configuration of the devices 170A, 172A, 130A, and 110 are substantially similar to the block diagram 200A of FIG. 2A, except that the pattern recognition interface 208A is located on the remote server 110 and a pattern comparison interface 208B is located on the local server. Accordingly, instead of the remote server 110 sending a copy of the collected medical device data 234 to the local server 130A as described with reference to block diagram 200A, the remote server 110 in block diagram 200B uses the pattern recognition interface 208A to identify patterns indicating adverse patient medical events. The remotes server 110 stores information on the patterns as pattern data 207A in memory 232 on the remote server 110. The remote server 110 then provides the pattern data over the wide area network 150 to the local server 130A. The local server 130A stores a copy of the pattern data 207B in memory 252. Using a pattern comparison interface, the local server 130A compares the patterns from the pattern data 207B that are indicative of a potential adverse patient medical event with real-time patient data from the medical device 170A. If a pattern match is identified, a notification regarding the adverse patient medical event is sent to the central monitor 172A and optionally to the medical device 170A.

Figure 3A:
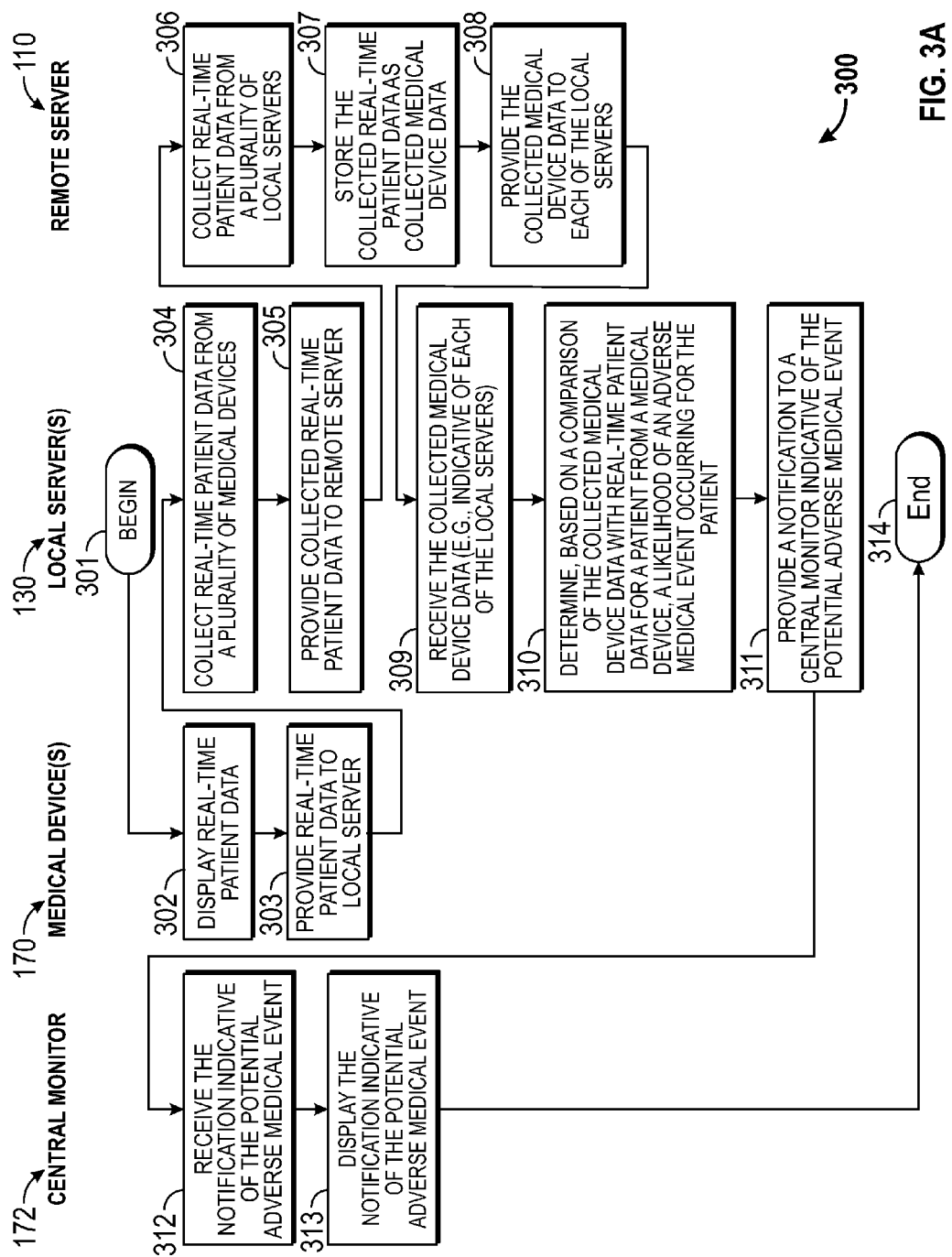
FIG. 3A illustrates an example process for providing predictive notifications to a monitoring device using the example medical device, central monitor, local server, and remote server of FIG. 2A.

FIG. 3A illustrates an example process 300 for providing predictive notifications to a monitoring device 170 using the example medical device 170A, local server 130A, and remote server 110 of FIG. 2A. While FIG. 3A is described with reference to FIG. 2A, it should be noted that the process steps of FIG. 3A may be performed by other systems.

The process 300 proceeds from beginning 301 to step 302 with a medical device 170 displaying real-time patient data. In step 303, the medical device 170 provides the real-time patient data to a local server 130 using a local area network 250.

Turning to the local server 130, in step 304, the local server 130 collects real-time patient data from each medical device 170 to which the local server 130 is connected. In step 305 the local server 130 provides the collected real-time patient data from each of the medical devices 170 to the remote server 110.

Turning to the remote server 110, in step 306 the remote server 110 collects the real-time patient data from each of the local servers 130 to which it is connected over the wide area network 150. In step 307, the remote server 110 stores the collected real-time patient data as collected medical device data 234. The remote server 110 then provides the collected medical device data 234 to each of the local servers 130 in step 308.

Returning to the local server 130, the local server 130 receives the collected medical device data 234 in step 309. In step 310, the local server 130 determines, based on a comparison of the collected medical device data 234 with real-time patient data for a patient from a medical device 170, a likelihood of a potential adverse medical event occurring for the patient. If such a potential adverse medical event is likely, then the local server 130 in step 311 provides a notification to the central monitor 172A. A notification can also be provided to the medical device 170 for the patient.

Turning to the central monitor 172A, the central monitor 172A receives the notification indicative of the potentially adverse medical event in step 312. In step 313, the medical device 170 displays the notification so that, for example, a person, such as a physician or pharmacist, can take appropriate action. The process 300 then ends on step 314.

FIG. 3A sets forth an example process 300 for providing predictive notifications to a monitoring device 170 using the example medical device 170A, central monitor 172A, local server 130A, and remote server 110 of FIG. 2A. An example will now be described using the example process 300 of FIG. 3A and a medical device 170A at location one 102 that is an infusion pump system administering a medication to patient BU453627 at location one 102.

The process 300 proceeds from beginning 301 to step 302 with each of a plurality of infusion pump systems 170A displaying real-time patient data, including the name of a medication being infused, medication amount, medication volume to be infused, and a rate of infusion. Other real-time patient data being monitored by the infusion pump system 170A but not being displayed includes the patient's $CO_2$ level, $O_2$ level, and heart rate. In step 303, the infusion pump system 170A provides the patient's real-time $CO_2$ level, $O_2$ level, heart rate data, and adverse medical event history to a local server 130 using a wireless (e.g., Wi-Fi) local area network 250.

Turning to the local server 130, in step 304, the local server 130 collects each patient's real-time $CO_2$ level, $O_2$ level, and heart rate data from corresponding infusion pump systems 170A to which the local server 130 is connected over the wireless local area network 250. In step 305 the local server 130 provides each of the patient's real-time $CO_2$ level, $O_2$ level, heart rate data, and adverse medical event history to the remote server 110.

Turning to the remote server 110, in step 306 the remote server 110 collects each patient's real-time $CO_2$ level, $O_2$ level, heart rate data, and adverse medical event history from each of the local servers 130 to which the remote server 110 is connected over the wide area network 150.

In step 307, the remote server 110 stores the collected real-time patient data as collected medical device data 234. The collected medical device data 234 includes $CO_2$ level, $O_2$ level, heart rate data, and adverse medical event history data for a plurality of patients. In one instance, the collected adverse medical event history indicates that a certain patient suffered from apnea, and in another instance that another patient suffered a seizure. The remote server 110 provides the collected medical device data 234 to each of the local servers 130 in step 308.

Returning to the local server 130, the local server 130 receives the collected medical device data 234 in step 309. In step 310, a pattern recognition interface 208 of the local server 130 determines, based on a comparison of the collected medical device data 234 with real-time patient data for a patient from a infusion pump system 170A, a likelihood of adverse medical events occurring for a patient as provided in the example illustration 400 of FIG. 4A.

FIG. 4A provides an exemplary multi-dimensional look up table 400 that identifies correlations between certain parameters and the occurrence of a potential adverse patient medical event. The pattern recognition interface 208 creates the multi-dimensional look up table 400 where per each combination of the parameters 402, 404, 406, and 408 displayed, the number of times an alert has occurred can be indicated. The pattern recognition interface 208 analyzes the look up table 400 to identify whether a current pattern of real-time data for a patient is similar to or the same as a pattern identified in the look up table 400.

Specifically, with reference to the look up table 400, the pattern recognition interface 208 determines that based on the collected medical device data 234, if a patient's current $CO_2$ level 404 is less than 50% 412, the patient's current $O_2$ level 406 is between 60%-88% 414, and the patient's heart rate 408 is lower than 50 beats per minute 416, then it is likely the patient will suffer a potential adverse medical event 402 of apnea 410. The pattern recognition interface 208 also determines that based on the collected medical device data 234, if a patient's current $CO_2$ level 404 is less than 50% 420 and the patient's current $O_2$ level 406 is less than 60% 422, then it is 80% likely the patient will suffer a potential adverse medical event 402 of a seizure 418. In step 310 the pattern recognition interface 208 further determines that real-time patient data for patient BU453627 at location one 102 indicates the patient currently has a $CO_2$ level of 40% and an $O_2$ level of 57%, and that therefore patient BU453627 is more likely to suffer from a seizure 418.

The local server 130 in step 311 provides a notification to a central monitor 172A, as provided in the example illustration of FIG. 4B. In step 312, the central monitor 172A receives the notification indicative of the potentially adverse medical event in step 312. In step 313, the central monitor 172A provides a display of the current infusion status of each of the infusion pump systems 170A at location one 102 to which the local server 130A is connected that includes the notification, if appropriate. The current infusion status provides information for each infusion pump system 170A, including a patient identification 432, infusion profile 434, infused medication name 436, medication amount 438, volume of medication to be infused (VTBI) 440, whether there is an alert 442 for the infusion pump system 170A, medication dose 446, medication infusion rate 448, estimate time until the infusion supply becomes empty 450, estimated volume of the medication remaining 452, infusion status 454, time of last update 456, and whether the information for the infusion pump system 170A is indicated as being high priority 458. Two of the listed infusion pump systems 170A, namely the first two listed infusion pump systems 468 and 460, have associated alerts 442 and are therefore designated as high priority 458. The second listed infusion pump system 460, namely the infusion pump system associated with patient identification BU453627 462, indicates that the patient BU453627 is receiving cyclosporine and that an alert is associated with the infusion of cyclosporine to patient BU453627 using the second listed infusion pump system 460. When selected (e.g., by clicking on the alert indicator), the alert indicates that patient BU453627 is more likely to suffer a seizure because patient BU453627's $CO_2$ level is less than 50% and the patient's current $O_2$ level is less than 60%.

In steps 311-313, the notification can be provided to the infusion pump system 170A of patient BU453627 as well. The medical device 170A displays the notification 482 as provided in the example illustration of FIG. 4C. The notification 482 displayed on the of the infusion pump system 170A states: "WARNING: Adverse Patient Event Expected. Low $CO_2$ and $O_2$ parameters indicate a 80% likelihood of seizure." The process 300 then ends on step 314.

Figure 3B:
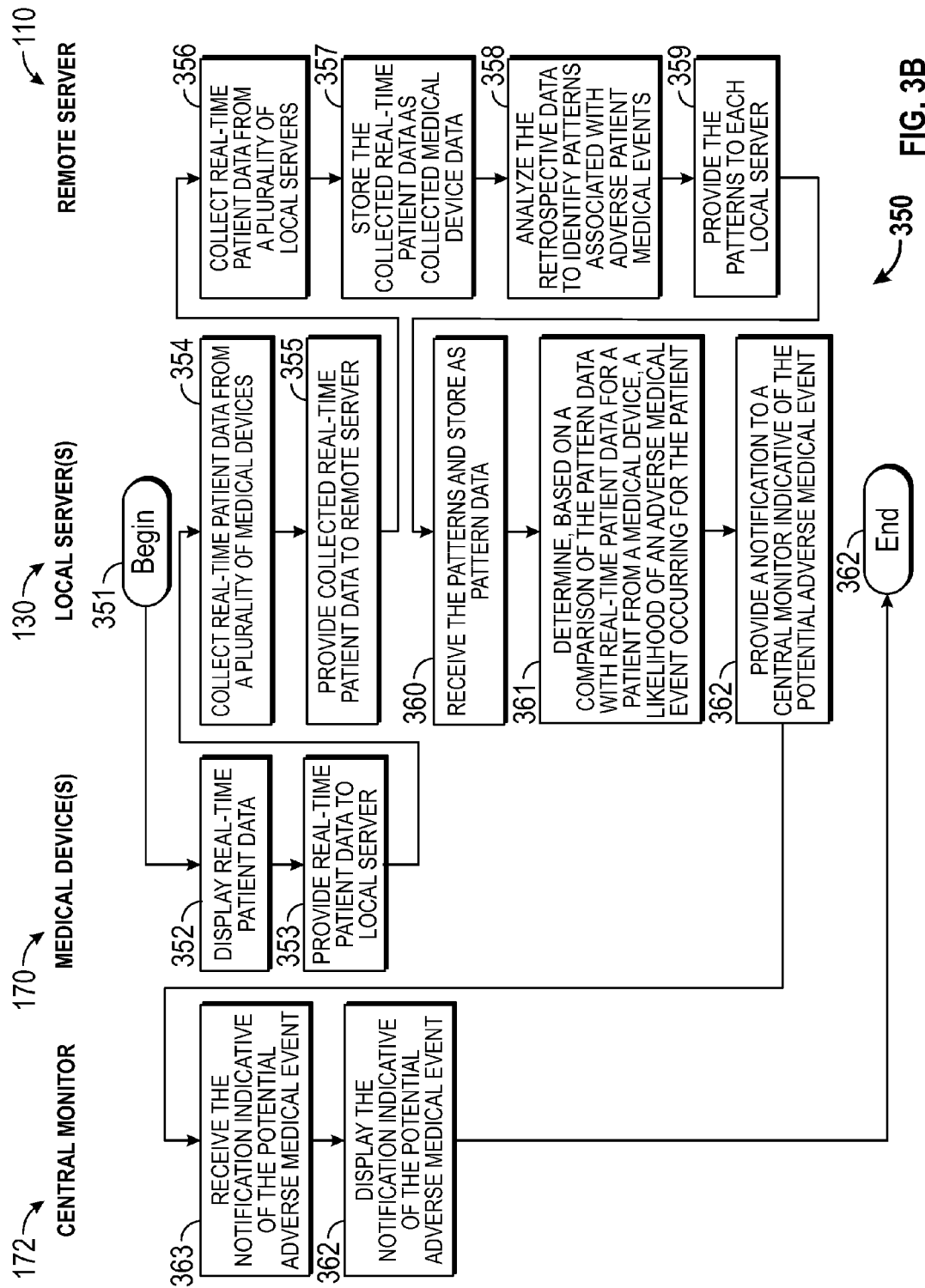
FIG. 3B illustrates an example process for providing predictive notifications to a monitoring device using the example medical device, central monitor, local server, and remote server of FIG. 2B.

FIG. 3A and FIGS. 4A-4C provided one example process 350 for providing predictive notifications to a monitoring device using the example medical device, central monitor, local server, and remote server of FIG. 2A, where the pattern recognition interface 208 is located on the local server 130A. FIG. 3B illustrates an example process 350 for providing predictive notifications to a monitoring device using the example medical device, central monitor, local server, and remote server of FIG. 2B, where the pattern recognition interface is located on the remote server 110. While FIG. 3B is described with reference to FIG. 2B, it should be noted that the process steps of FIG. 3B may be performed by other systems.

The process 350 proceeds from beginning 351 to step 352 with a medical device 170 displaying real-time patient data. In step 353, the medical device 170 provides the real-time patient data to a local server 135 using a local area network 250.

Turning to the local server 135, in step 354, the local server 135 collects real-time patient data from each medical device 170 to which the local server 135 is connected. In step 355 the local server 135 provides the collected real-time patient data from each of the medical devices 170 to the remote server 110.

Turning to the remote server 110, in step 356 the remote server 110 collects the real-time patient data from each of the local servers 135 to which it is connected over the wide area network 150. In step 357, the remote server 110 stores the collected real-time patient data as collected medical device data 234. In step 358, the remote server 110 analyzes the collected medical device data 234 to identify patterns associated with adverse patient medical events. The remote server 110 then provides the identified patterns 207A to each of the local servers 135 in step 359.

Returning to the local server 135, the local server 135 receives the patterns 207A in step 360 and stores a local copy of the patterns as pattern data 207B. In step 361, a pattern comparison interface 208B on the local server 135 determines, based on a comparison of the pattern data 207B with real-time patient data for a patient from a medical device 170, a likelihood of a potential adverse medical event occurring for the patient. If such a potential adverse medical event is likely, then the local server 135 in step 362 provides a notification to the central monitor 172 for the patient. The notification can also be provided to the medical device 170 as well.

Turning to the central monitor 172, the central monitor 172 receives the notification indicative of the potentially adverse medical event in step 363. In step 364, the central monitor 172 displays the notification. The process 350 then ends on step 365.

FIG. 3B sets forth an example process 350 for providing predictive notifications to a monitoring device 170 using the example medical device 170A, local server 130A, and remote server 110 of FIG. 2B. An example will now be described using the example process 350 of FIG. 3B and a medical device 170A at location one 102 that is an infusion pump system administering a medication to a new patient at location one 102.

The process 350 proceeds from beginning 351 to step 352 with each of a plurality of infusion pump systems 170A displaying real-time patient data, including the name of a medication being infused, medication amount, medication volume to be infused, and a rate of infusion. Other real-time patient data being monitored by the infusion pump system 170A but not being displayed includes the patient's $CO_2$ level, $O_2$ level, and heart rate. In step 353, the infusion pump system 170A provides the patient's real-time $CO_2$ level, $O_2$ level, heart rate data, and adverse medical event history to a local server 135 using a wireless (e.g., Wi-Fi) local area network 250.

Turning to the local server 135, in step 354, the local server 135 collects each patient's real-time $CO_2$ level, $O_2$ level, and heart rate data from corresponding infusion pump systems 170A to which the local server 135 is connected over the wireless local area network 250. In step 355 the local server 135 provides each of the patient's real-time $CO_2$ level, $O_2$ level, heart rate data, and adverse medical event history to the remote server 110.

Turning to the remote server 110, in step 356 the remote server 110 collects each patient's real-time $CO_2$ level, $O_2$ level, heart rate data, and adverse medical event history from each of the local servers 135 to which the remote server 110 is connected over the wide area network 150.

In step 357, the remote server 110 stores the collected real-time patient data as collected medical device data 234. The collected medical device data 234 includes $CO_2$ level, $O_2$ level, heart rate data, and adverse medical event history data for a plurality of patients. In one instance, the collected adverse medical event history indicates that a certain patient suffered from apnea, and in another instance that another patient suffered a seizure.

In step 358, a pattern recognition interface 208A of the remote server 110 analyzes the collected medical device data 234 to identify patterns associated with adverse patient medical events. The identified patterns are in provided in the example illustration 400 of FIG. 4A discussed above. The remote server 110 then provides the identified patterns 207A to each of the local servers 135 in step 359.

Returning to the local server 135, the local server 135 receives the patterns 207A in step 360 and stores a local copy of the patterns as pattern data 207B. In step 361, a pattern comparison interface 208B on the local server 135 determines, based on a comparison of the pattern data 207B with real-time patient data for the new patient at location one 102 from a medical device 170, that it is likely a potential adverse medical event will occur for the new patient. Specifically, with reference to the look up table 400, the pattern recognition interface 208 determines that real-time patient data for the new patient at location one 102 indicates the patient currently has a $CO_2$ level of 47% and an $O_2$ level of 67%, and that therefore that the new patient is likely to suffer from apnea. The local server 135 in step 362 provides a notification to the central monitor 172 indicating the likely apnea for the new patient.

Turning to the central monitor 172, the central monitor 172 receives the notification indicative of apnea for the new patient in step 363. In step 364, the central monitor 172 displays the notification, thereby providing a warning about the potential apnea the new patient may suffer. The process 350 then ends on step 365.

Figure 5:
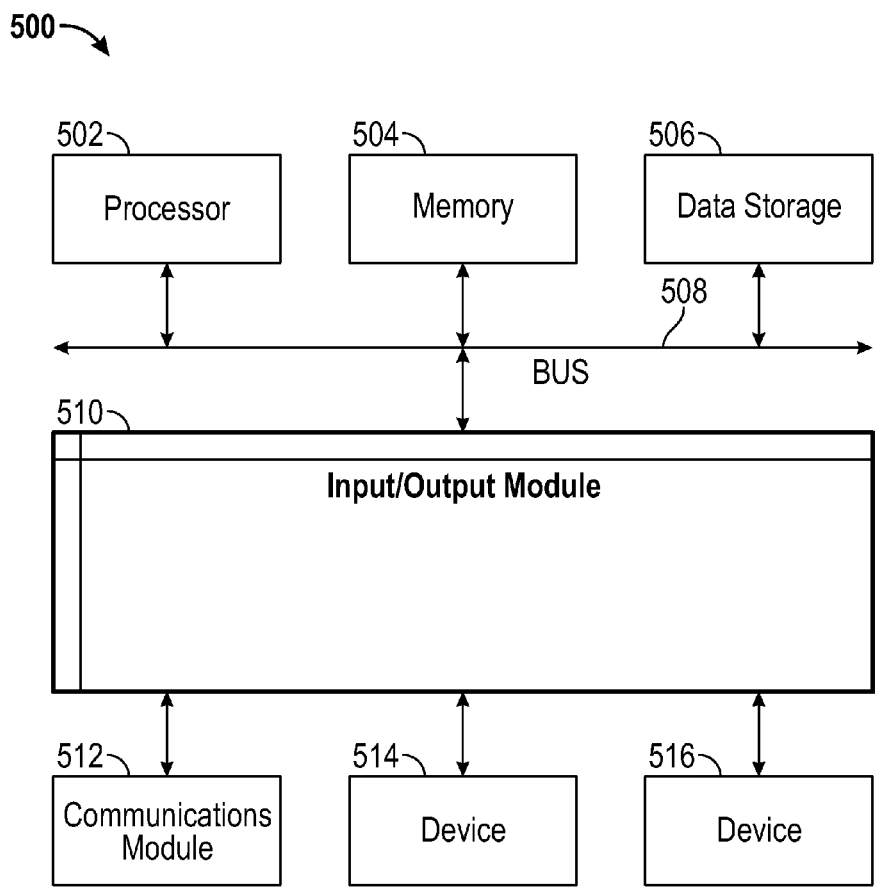
FIG. 5 is a block diagram illustrating an example computer system with which the local servers and remote server of FIGS. 1, 2A, and 2B can be implemented.

FIG. 5 is a block diagram illustrating an example computer system 500 with which the local servers 130A-C and remote server 110 of FIGS. 1, 2A, and 2B can be implemented. In certain aspects, the computer system 500 may be implemented using hardware or a combination of software and hardware, either in a dedicated server, or integrated into another entity, or distributed across multiple entities.

Computer system 500 (e.g., local servers 130A-C and remote server 110) includes a bus 508 or other communication mechanism for communicating information, and a processor 502 (e.g., processor 254 and 236) coupled with bus 508 for processing information. By way of example, the computer system 500 may be implemented with one or more processors 502. Processor 502 may be a general-purpose microprocessor, a microcontroller, a Digital Signal Processor (DSP), an Application Specific Integrated Circuit (ASIC), a Field Programmable Gate Array (FPGA), a Programmable Logic Device (PLD), a controller, a state machine, gated logic, discrete hardware components, or any other suitable entity that can perform calculations or other manipulations of information.

Computer system 500 can include, in addition to hardware, code that creates an execution environment for the computer program in question, e.g., code that constitutes processor firmware, a protocol stack, a database management system, an operating system, or a combination of one or more of them stored in an included memory 504 (e.g., memory 252 and 232), such as a Random Access Memory (RAM), a flash memory, a Read Only Memory (ROM), a Programmable Read-Only Memory (PROM), an Erasable PROM (EPROM), registers, a hard disk, a removable disk, a CD-ROM, a DVD, or any other suitable storage device, coupled to bus 508 for storing information and instructions to be executed by processor 502. The processor 502 and the memory 504 can be supplemented by, or incorporated in, special purpose logic circuitry.

The instructions may be stored in the memory 504 and implemented in one or more computer program products, i.e., one or more modules of computer program instructions encoded on a computer readable medium for execution by, or to control the operation of, the computer system 500, and according to any method well known to those of skill in the art, including, but not limited to, computer languages such as data-oriented languages (e.g., SQL, dBase), system languages (e.g., C, Objective-C, C++, Assembly), architectural languages (e.g., Java, .NET), and application languages (e.g., PHP, Ruby, Perl, Python). Instructions may also be implemented in computer languages such as array languages, aspect-oriented languages, assembly languages, authoring languages, command line interface languages, compiled languages, concurrent languages, curly-bracket languages, dataflow languages, data-structured languages, declarative languages, esoteric languages, extension languages, fourth-generation languages, functional languages, interactive mode languages, interpreted languages, iterative languages, list-based languages, little languages, logic-based languages, machine languages, macro languages, metaprogramming languages, multiparadigm languages, numerical analysis, non-English-based languages, object-oriented class-based languages, object-oriented prototype-based languages, off-side rule languages, procedural languages, reflective languages, rule-based languages, scripting languages, stack-based languages, synchronous languages, syntax handling languages, visual languages, wirth languages, embeddable languages, and xml-based languages. Memory 504 may also be used for storing temporary variable or other intermediate information during execution of instructions to be executed by processor 502.

A computer program as discussed herein does not necessarily correspond to a file in a file system. A program can be stored in a portion of a file that holds other programs or data (e.g., one or more scripts stored in a markup language document), in a single file dedicated to the program in question, or in multiple coordinated files (e.g., files that store one or more modules, subprograms, or portions of code). A computer program can be deployed to be executed on one computer or on multiple computers that are located at one site or distributed across multiple sites and interconnected by a communication network. The processes and logic flows described in this specification can be performed by one or more programmable processors executing one or more computer programs to perform functions by operating on input data and generating output.

Computer system 500 further includes a data storage device 506 such as a magnetic disk or optical disk, coupled to bus 508 for storing information and instructions. Computer system 500 may be coupled via input/output module 510 to various devices (e.g., medical devices 170A-C). The input/output module 510 can be any input/output module. Example input/output modules 510 include data ports such as USB ports. The input/output module 510 is configured to connect to a communications module 512. Example communications modules 512 (e.g., communications module 256 and 238) include networking interface cards, such as Ethernet cards and modems. In certain aspects, the input/output module 510 is configured to connect to a plurality of devices, such as an input device 514 and/or an output device 516. Example input devices 514 include a keyboard and a pointing device, e.g., a mouse or a trackball, by which a user can provide input to the computer system 500. Other kinds of input devices 514 can be used to provide for interaction with a user as well, such as a tactile input device, visual input device, audio input device, or brain-computer interface device. For example, feedback provided to the user can be any form of sensory feedback, e.g., visual feedback, auditory feedback, or tactile feedback; and input from the user can be received in any form, including acoustic, speech, tactile, or brain wave input. Example output devices 516 include display devices, such as a LED (light emitting diode), CRT (cathode ray tube), or LCD (liquid crystal display) screen, for displaying information to the user.

According to one aspect of the present disclosure, the local servers 130A-C and remote server 110 can be implemented using a computer system 500 in response to processor 502 executing one or more sequences of one or more instructions contained in memory 504. Such instructions may be read into memory 504 from another machine-readable medium, such as data storage device 506. Execution of the sequences of instructions contained in main memory 504 causes processor 502 to perform the process steps described herein. One or more processors in a multi-processing arrangement may also be employed to execute the sequences of instructions contained in memory 504. In alternative aspects, hard-wired circuitry may be used in place of or in combination with software instructions to implement various aspects of the present disclosure. Thus, aspects of the present disclosure are not limited to any specific combination of hardware circuitry and software.

Various aspects of the subject matter described in this specification can be implemented in a computing system that includes a back end component, e.g., as a data server, or that includes a middleware component, e.g., an application server, or that includes a front end component, e.g., a client computer having a graphical user interface or a Web browser through which a user can interact with an implementation of the subject matter described in this specification, or any combination of one or more such back end, middleware, or front end components. The components of the system can be interconnected by any form or medium of digital data communication, e.g., a communication network. The communication network (e.g., local area network 250 and wide area network 150) can include, for example, any one or more of a personal area network (PAN), a local area network (LAN), a campus area network (CAN), a metropolitan area network (MAN), a wide area network (WAN), a broadband network (BBN), the Internet, and the like. Further, the communication network can include, but is not limited to, for example, any one or more of the following network topologies, including a bus network, a star network, a ring network, a mesh network, a star-bus network, tree or hierarchical network, or the like. The communications modules can be, for example, modems or Ethernet cards.

Computing system 500 can include clients and servers. A client and server are generally remote from each other and typically interact through a communication network. The relationship of client and server arises by virtue of computer programs running on the respective computers and having a client-server relationship to each other. Computer system 500 can be, for example, and without limitation, a desktop computer, laptop computer, or tablet computer. Computer system 500 can also be embedded in another device, for example, and without limitation, a mobile telephone, a personal digital assistant (PDA), a mobile audio player, a Global Positioning System (GPS) receiver, a video game console, and/or a television set top box.

The term "machine-readable storage medium" or "computer readable medium" as used herein refers to any medium or media that participates in providing instructions or data to processor 502 for execution. Such a medium may take many forms, including, but not limited to, non-volatile media, volatile media, and transmission media. Non-volatile media include, for example, optical disks, magnetic disks, or flash memory, such as data storage device 506. Volatile media include dynamic memory, such as memory 504. Transmission media include coaxial cables, copper wire, and fiber optics, including the wires that comprise bus 508. Common forms of machine-readable media include, for example, floppy disk, a flexible disk, hard disk, magnetic tape, any other magnetic medium, a CD-ROM, DVD, any other optical medium, punch cards, paper tape, any other physical medium with patterns of holes, a RAM, a PROM, an EPROM, a FLASH EPROM, any other memory chip or cartridge, or any other medium from which a computer can read. The machine-readable storage medium can be a machine-readable storage device, a machine-readable storage substrate, a memory device, a composition of matter effecting a machine-readable propagated signal, or a combination of one or more of them.

Systems, methods, and machine-readable media for providing predictive notifications to a monitoring device have been described. A server obtains real-time patient data for a patient from a medical device and compares the data to retrospective patient data for a plurality of patients. The retrospective patient data includes information on adverse patient medical events suffered by the plurality of patients. Based on the comparison, the server identifies whether the real-time patient data from the medical device indicates that the patient is likely to suffer a potential adverse medical event. The comparison can be done using a pattern matching algorithm. If it is determined that the patient is likely to suffer a potential adverse medical event, the server provides a notification to the medical device and other appropriate devices with information on the potential adverse patient medical event.

As used herein, the phrase "at least one of" preceding a series of items, with the terms "and" or "or" to separate any of the items, modifies the list as a whole, rather than each member of the list (i.e., each item). The phrase "at least one of" does not require selection of at least one item; rather, the phrase allows a meaning that includes at least one of any one of the items, and/or at least one of any combination of the items, and/or at least one of each of the items. By way of example, the phrases "at least one of A, B, and C" or "at least one of A, B, or C" each refer to only A, only B, or only C; any combination of A, B, and C; and/or at least one of each of A, B, and C.

Furthermore, to the extent that the term "include," "have," or the like is used in the description or the claims, such term is intended to be inclusive in a manner similar to the term "comprise" as "comprise" is interpreted when employed as a transitional word in a claim.

The word "exemplary" is used herein to mean "serving as an example, instance, or illustration." Any embodiment described herein as "exemplary" is not necessarily to be construed as preferred or advantageous over other embodiments.

A reference to an element in the singular is not intended to mean "one and only one" unless specifically stated, but rather "one or more." All structural and functional equivalents to the elements of the various configurations described throughout this disclosure that are known or later come to be known to those of ordinary skill in the art are expressly incorporated herein by reference and intended to be encompassed by the subject technology. Moreover, nothing disclosed herein is intended to be dedicated to the public regardless of whether such disclosure is explicitly recited in the above description.

While this specification contains many specifics, these should not be construed as limitations on the scope of what may be claimed, but rather as descriptions of particular implementations of the subject matter. Certain features that are described in this specification in the context of separate embodiments can also be implemented in combination in a single embodiment. Conversely, various features that are described in the context of a single embodiment can also be implemented in multiple embodiments separately or in any suitable subcombination. Moreover, although features may be described above as acting in certain combinations and even initially claimed as such, one or more features from a claimed combination can in some cases be excised from the combination, and the claimed combination may be directed to a subcombination or variation of a subcombination.

Similarly, while operations are depicted in the drawings in a particular order, this should not be understood as requiring that such operations be performed in the particular order shown or in sequential order, or that all illustrated operations be performed, to achieve desirable results. In certain circumstances, multitasking and parallel processing may be advantageous. Moreover, the separation of various system components in the aspects described above should not be understood as requiring such separation in all aspects, and it should be understood that the described program components and systems can generally be integrated together in a single software product or packaged into multiple software products.

The subject matter of this specification has been described in terms of particular aspects, but other aspects can be implemented and are within the scope of the following claims. For example, the actions recited in the claims can be performed in a different order and still achieve desirable results. As one example, the processes depicted in the accompanying figures do not necessarily require the particular order shown, or sequential order, to achieve desirable results. In certain implementations, multitasking and parallel processing may be advantageous. Other variations are within the scope of the following claims.

These and other implementations are within the scope of the following claims.

What is claimed is:

1. A system for providing predictive notifications to a monitoring device, the system comprising:
a memory comprising retrospective patient data collected from a plurality of medical devices; and
a processor configured to:
receive retrospective patient data collected for a plurality of patients from a plurality of medical devices, including respective values for at least two different physiological levels monitored while a medication was provided to the plurality of patients;
receive adverse medical event history for the plurality of patients;
determine, based on the received retrospective patient data and the received adverse medical event history, a plurality of patterns of parameter values associated with medication information and physiological levels and that correspond to respective medical conditions occurring during administration of a medication;
receive, from a patient medical device, current patient parameter values associated with information on a current medication provided to a current patient and at least two different physiological levels monitored during administration of the current medication;
determine, based on a comparison of the retrospective patient data with the current patient parameter values from the patient medical device, a likelihood of a potential specific medical condition occurring for the current patient; and
provide a notification indicative of the potential specific medical condition for the current patient to the patient medical device,
wherein the comparison of the retrospective patient data comprises comparing the current patient parameter values associated with the information on the current medication and the at least two different physiological levels with a selection of at least one stored pattern of parameter values from the plurality of patterns of parameter values.

2. The system of claim 1, wherein the processor is configured to determine the likelihood of the potential specific medical condition occurring for the current patient using a pattern matching algorithm, and wherein each parameter in each pattern comprises a range of values determined based on the plurality of patients for that pattern.

3. The system of claim 1, wherein each of the determined plurality of patterns further comprises values indicating at least two of drug name, drug concentration, $CO_2$ degree of change over time, and $O_2$ degree of change over time.

4. The system of claim 2, wherein the pattern matching algorithm comprises at least one of keypoint matching, elementary image processing, histogram matching, string searching, approximate string matching.

5. The system of claim 2, wherein the current patient parameter values comprises real-time current patient data, and wherein the potential specific medical condition comprises one or more of a heart attack, a seizure, or apnea.

6. The system of claim 1, wherein the notification includes information on how to configure the medical device in order to reduce a likelihood of an occurrence of the potential specific medical condition.

7. The system of claim 1, wherein the retrospective patient data is received from a server that is configured to collect, over a network, the retrospective patient data from the plurality of medical devices across a plurality of health institutions.

8. The system of claim 7, wherein the received retrospective patient data is a subset of the retrospective patient data collected from the plurality of medical devices across the plurality of health institutions.

9. The system of claim 1, wherein the retrospective patient data comprises patient data that is older than one day, and wherein the current patient parameter values comprises patient data that is obtained from a patient within at least one of a past 5 seconds, 10 seconds, 15 seconds, 30 seconds, one minute, two minutes, five minutes, ten minutes, thirty minutes, or an hour.

10. The system of claim 1, wherein the each of the plurality of medical devices and the patient medical device comprises one of an infusion pump system, ventilator system, or a physiological statistic monitor.

11. The system of claim 1, wherein each of the plurality of patterns is pre-determined to indicate a particular medical condition suffered by a group of patients based on respective ranges of parameter values associated with medication information and physiological levels for the group of patients during an administration of the current medication, and wherein each of the different physiological levels includes a different one of a $CO_2$ level, an $O_2$ level, and a heart rate.

12. A method for providing predictive notifications to a monitoring device, the method comprising:
receiving retrospective patient data collected for a plurality of patients from a plurality of medical devices, including respective values for at least two different physiological levels monitored while a medication was provided to the plurality of patients;
receiving adverse medical event history for the plurality of patients;
determining, based on the received retrospective patient data and the received adverse medical event history, a plurality of patterns of parameter values associated with medication information and physiological levels and that correspond to respective medical conditions occurring during administration of a medication;
receive, from a patient medical device, current patient parameter values associated with information on a current medication provided to a current patient and at least two different physiological levels monitored during administration of the current medication;
determining, based on a comparison of the retrospective patient data with the current patient parameter values from the patient medical device, a likelihood of a potential specific medical condition occurring for the current patient; and
providing a notification indicative of the potential specific medical condition for the current patient to the patient medical device, wherein the comparison of the retrospective patient data with the current patient parameter values comprises selecting at least one stored pattern of parameter values from the plurality of patterns of parameter values based on a comparison of the current patient parameter values associated with the information on the current medication and the at least two different physiological levels with parameters of the selected at least one stored pattern.

13. The method of claim 12, wherein the determination of the likelihood of the potential specific medical condition occurring for the current patient is made using a pattern matching algorithm.

14. The method of claim 12, wherein each of the determined plurality of patterns comprises values indicating at least two of drug name, drug concentration, $CO_2$ degree of change over time, and $O_2$ degree of change over time.

15. The method of claim 13, wherein the pattern matching algorithm comprises at least one of keypoint matching, elementary image processing, histogram matching, string searching, approximate string matching.

16. The method of claim 12, wherein the notification includes information on how to configure the medical device in order to reduce a likelihood of an occurrence of the potential specific medical condition.

17. The method of claim 12, wherein the retrospective patient data is received from a server that is configured to collect, over a network, the retrospective patient data from the plurality of medical devices across a plurality of health institutions.

18. The method of claim 17, wherein the received retrospective patient data is a subset of the retrospective patient data collected from the plurality of medical devices across the plurality of health institutions.

19. The method of claim 12, wherein the retrospective patient data comprises patient data that is older than one day, and wherein the current patient parameter values comprises patient data that is obtained from a patient within at least one of a past 5 seconds, 10 seconds, 15 seconds, 30 seconds, one minute, two minutes, five minutes, ten minutes, thirty minutes, or an hour.

20. The method of claim 12, wherein each of the plurality of medical devices and the patient medical device comprises one of an infusion pump system, ventilator system, or a physiological statistic monitor.

21. The method of claim 12, wherein each of the plurality of patterns is pre-determined to indicate a particular medical condition suffered by a group of patients based on respective ranges of parameter values associated with medication information and physiological levels for the group of patients during an administration of the current medication, and wherein each of the different physiological levels includes a different one of a $CO_2$ level, an $O_2$ level, and a heart rate.

22. A non-transitory machine-readable storage medium comprising machine-readable instructions for causing a processor to execute a method for providing predictive notifications, the method comprising:
receiving retrospective patient data collected for a plurality of patients from a plurality of medical devices, including respective values for a least two different physiological levels monitored while a medication was provided to the plurality of patients;
receiving adverse medical event history for the plurality of patients;
determining, based on the received retrospective patient data and the received adverse medical event history, a plurality of patterns of parameter values associated with medication information and physiological levels and that correspond to respective medical conditions occurring during administration of a medication;
receive, from a patient medical device, current patient parameter values associated with information on a current medication provided to a current patient and at least two different physiological levels monitored during administration of the current medication;
determining, based on a comparison of the retrospective patient data with the current patient parameter values from the patient medical device, a likelihood of a potential adverse medical condition, comprising one or more of a seizure, a heart attack, or apnea, occurring for the patient; and
providing a notification indicative of the potential adverse medical condition for the current patient to the patient medical device, wherein the comparison of the retrospective patient data with the current patient parameter values comprises selecting at least one stored pattern of parameter values from the plurality of patterns of parameter values based on a comparison of the current patient parameter values associated with the information on the current medication and the at least two different physiological levels with parameters of the selected at least one stored pattern.

23. The machinereadable storage medium of claim 22, wherein each of the plurality of patterns is predetermined to indicate a particular medical condition suffered by a group of patients based on respective ranges of parameter values associated with medication information and physiological levels for the group of patients during an administration of the current medication, and wherein each of the different physiological levels includes a different one of a $CO_2$ level, an $O_2$ level, and a heart rate.

* * * * *